(12) United States Patent
Gardner et al.

(10) Patent No.: US 9,096,875 B2
(45) Date of Patent: Aug. 4, 2015

(54) BICARBONATE TRIGGER FOR INDUCING LIPID ACCUMULATION IN ALGAL SYSTEMS

(75) Inventors: Robert Gardner, Bozeman, MT (US); Brent Peyton, Bozeman, MT (US); Keith E. Cooksey, Manhattan, MT (US)

(73) Assignee: Montana State University, Bozeman, MT (US)

( * ) Notice: Subject to any disclaimer, the term of this patent is extended or adjusted under 35 U.S.C. 154(b) by 0 days.

(21) Appl. No.: 13/825,934

(22) PCT Filed: Sep. 26, 2011

(86) PCT No.: PCT/US2011/053238
§ 371 (c)(1),
(2), (4) Date: Jul. 24, 2013

(87) PCT Pub. No.: WO2012/040698
PCT Pub. Date: Mar. 29, 2012

(65) Prior Publication Data
US 2013/0295623 A1    Nov. 7, 2013

Related U.S. Application Data

(60) Provisional application No. 61/386,260, filed on Sep. 24, 2010, provisional application No. 61/434,675, filed on Jan. 20, 2011.

(51) Int. Cl.
*C12P 7/64* (2006.01)
*C12N 1/12* (2006.01)

(52) U.S. Cl.
CPC ... *C12P 7/64* (2013.01); *C12N 1/12* (2013.01); *C12P 7/6463* (2013.01)

(58) Field of Classification Search
USPC .................................. 435/134, 257.5; 47/1.4
See application file for complete search history.

(56) References Cited

U.S. PATENT DOCUMENTS

| 8,569,040 B1 * | 10/2013 | Kroger et al. | 435/257.1 |
| 2009/0130706 A1 | 5/2009 | Berzin et al. | |
| 2010/0112649 A1 * | 5/2010 | Willson et al. | 435/134 |

FOREIGN PATENT DOCUMENTS

| WO | WO 2009/005496 A1 | | 1/2009 |
| WO | WO 2009/094440 | * | 7/2009 |
| WO | WO 2009/094440 A1 | | 7/2009 |
| WO | WO 2009/111513 A1 | | 9/2009 |

OTHER PUBLICATIONS

Gardner R. et al. Use of Sodium Bicarbonate to Stimulate Triacylglycerol Accumulation in the Chlorophyte Scenedesmus sp . . . J Applied Phycology 24(5)1311-1320, Oct. 2012.*
Guckert J. et al. Triglyceride Accumulation and Fatty Acid Profile Changes in Chlorella During High pH Induced Cell Cycle Inhibition. J of Phycology 26(1)72-79, Mar. 1990. Legible copy provided.*
Brown et al., "Effects of harvest stage and light on the biochemical composition of the diatom *Thalassiosira pseudonana*," J. Phycol. 32:64-73 (1996).
Claquin et al., "Relationship between photosynthetic metabolism and cell cycle in a synchronized culture of the marine alga *Cylindrotheca fusiformis* (Bacillariophyceae)," Eur. J. Phycol. 39:33-41 (2004).
Dean et al., "Using FTIR spectroscopy for rapid determination of lipid accumulation in response to nitorgen limitation in freshwater microalgae," Bioresource Technol. 101:4499-4507 (2010).
Gardner et al., "Medium pH and nitrate concentration effects on accumulation of triacylglycerol in two members of the chlorophyta," J. Appl. Phycol. 23:1005-1016 (2010).
Gardner et al., "Use of sodium bicarbonate to stimulate triacylglycerol accumulation in the chlorophytes and the diatom," J. Appl. Phycol. 24:1311-1320 (2012).
Guckert et al., "Triglyceride Accumulation and Fatty Acid Profile Change in Chlorella (Chlorophyta) During High pH-Induced Cell Cycle Inhibition," J. Phycol. 26:72-79 (1990).
Mansour et al., "The effect of growth phase on the lipid class, fatty acid and sterol composition in the marine dinoflagellate, *Gymnodinium* sp. in batch culture," Phytochem. 63:145-153 (2003).
Supplementary European Search Report. EP appl. No. 11827712.8, 12 pages (Feb. 28, 2014).
International Search Report based on International Patent Application No. PCT/US2011/053238, mailed on Feb. 16, 2012.

* cited by examiner

*Primary Examiner* — Ralph Gitomer
(74) *Attorney, Agent, or Firm* — Cooley LLP

(57) ABSTRACT

The present invention provides bicarbonate containing and/or bicarbonate-producing compositions and methods to induce lipid accumulation in an algae growth system, wherein the algae growth system is under light-dark cycling condition. By adding said compositions at a specific growth stage, said methods lead to much higher lipid accumulation and/or significantly reduced total time required for accumulating lipid in the algae growth system.

10 Claims, 19 Drawing Sheets

BICARBONATE TRIGGER FOR INDUCING LIPID ACCUMULATION IN ALGAL SYSTEMS

CROSS-REFERENCE TO RELATED APPLICATIONS

This application claims the benefit of, and is a National Stage Entry of International Patent Application No. PCT/US2011/053238, filed Sep. 26, 2011, which claims priority to U.S. Provisional Application Ser. No. 61/386,260, filed Sep. 24, 2010, and U.S. Provisional Application Ser. No. 61/434,675, filed Jan. 20, 2011. International Patent Application No. PCT/US2011/053238 and U.S. Provisional Patent Application Nos. 61/386,260 and 61/434,675 which are herein incorporated by reference in their entirety entireties.

GOVERNMENT RIGHTS STATEMENT

This invention was made with government support under grant number DGE 0654336, awarded by National Science Foundation; grant number FA9550-09-1-0243, awarded by Air Force Office of Scientific Research; and grant number DE-FG36-08GO18161, awarded by US Department of Energy Office of Biomass Programs. The government has certain rights in the invention.

TECHNICAL FIELD

This application relates to compositions and methods to induce lipid accumulation in algal systems.

BACKGROUND

Biodiesel, diesel fuel made from a biological source such as microalgal oil or soybean oil, is an important alternative to petroleum derived diesel. Algae are potentially a superior source of oil than plants such as soybeans because they are theoretically capable of producing more oil per acre of land/space required to grow them: for example, algae could theoretically produce 20-times the oil per acre than soybeans. Algae can be grown on non-agricultural land using little water, avoiding controversy over the diversion of food and food-production resources to fuel production when there are starving people in the world.

Triacylglycerol (TAG) is the precursor molecule of biodiesel, defined as fuel comprised of fatty acid methyl esters, and algal growth systems have the potential to produce TAG to a larger degree than land-based plant systems. Furthermore, particular fatty acid chains are desirable for altering the physical characteristics of biodiesel (e.g. gel point) or for secondary market use (e.g. nutraceutical market—omega-3 fatty acids).

SUMMARY OF THE INVENTION

The present invention provides methods of inducing lipid accumulation in an algae growth system. In some embodiments, the methods comprise adding one or more composition into the algae growth system, wherein the composition can influence the ability of an algae cell to complete a growth cycle, but is not completely toxic and does not result in cell death. In some embodiments, the composition comprises bicarbonate, and/or one or more compounds that provide bicarbonate after the composition (i.e., a bicarbonate containing and/or bicarbonate producing composition) is added into the algae growth system.

The present invention is based on the instant discovery that addition of bicarbonate ($HCO_3$), at key growth points, is a metabolic trigger for inducing accumulation of TAG in algal growth systems. Furthermore, by using this bicarbonate trigger, TAG is produced to a much larger degree (tenfold so far) and total culture time is decreased (by several days) when compared to non-triggered systems. Therefore, the present invention discloses compositions and methods of utilizing this triggering mechanism, which has strong industrial application in biofuel production or secondary market production when algal growth systems are used.

In some embodiments, the algae growth system is under light-dark cycling conditions or under continuous dark conditions. In some embodiments, said methods comprise adding a composition when algae cells in the growth system are in exponential growth stage, but prior to nutrition depletion of the growth system and/or environmental factor changes of the growth system which induces lipid accumulation. In some embodiments, the lipid accumulation comprises TAG accumulation. In some embodiments, the nutrition is nitrate, ammonia/ammonium, urea, phosphate, sodium thiosulphate, silica, iron, or a combination thereof. In some embodiments, the environmental factor is concentration of $CO_2$, pH, light (e.g., light intensity, light quality, light compositions etc), temperature, or a combination thereof.

In some embodiments, algae cell growth/replication in the growth system is inhibited before, at the time, or after adding the composition. In some embodiments, the inhibiting step happens during exponential growth of algae in the system.

In some embodiments, the composition comprises bicarbonate, and/or one or more compounds that provide bicarbonate after the composition (i.e., a bicarbonate containing and/or bicarbonate producing composition) is added into the algae growth system. In some embodiments, the composition further comprises one or more compounds that can increase the pH of the algae growth system. In some embodiments, the composition further comprises an inorganic nitrogen source (e.g., ammonium ($NH_4^+$) containing compounds, nitrite ($NO_2^-$) containing compounds, and nitrate ($NO_3^-$) containing compounds) and/or an organic nitrogen source (e.g., urea, hypoxanthine, guanine, ornithine, glucosamine, and lysine).

In some embodiments, the inhibiting step comprises an aeration shift of $CO_2$ concentration in the growth system from high to low, wherein the shift is sufficient to inhibit algae cell growth/replication partially, or completely. In some embodiments, the $CO_2$ concentration in the system after the shift from high to low is about 90%, about 80%, about 70%, about 60%, about 50%, about 40%, about 30%, about 20%, about 10%, about 5%, about 1%, about 0.1%, about 0.01%, about 0.001%, or less of the $CO_2$ concentration before the shift. The aeration shift of $CO_2$ concentration in the growth system from high to low is not required if the bicarbonate trigger is used for an ambient air sparged culture. Under such circumstances, the addition of bicarbonate inhibits algal replication.

In some embodiments, the algae are selected from the group consisting of *Scenedesmus* spp., diatoms (e.g., pennate diatoms), *Botryococcus* spp. (e.g., *B. braunii*), *Chlorella*, *Dunaliella* spp. (e.g., *D. tertiolecta*), *Gracilaria*, *Pleurochrysis* (e.g., *P. carterae*), *Chlorophyta*, and *Sargassum*. In some further embodiments, the *Scenedesmus* sp. is *Scenedesmus* WC-1 (WC-1) strain, the *Chlorophyta* is *Chlorophyta* sp. EN-2 (EN-2), and the diatom is diatom RGd-1 (RGd-1). In other embodiments, the algae may be *Scenedesmus* spp., diatoms (e.g., pennate diatoms), *Botryococcus* spp. (e.g., *B. braunii*), *Dunaliella* spp. (e.g., *D. tertiolecta*), *Gracilaria*, *Pleurochrysis* (e.g., *P. carterae*), *Chlorophyta*, and *Sargassum* but not *Chlorella*.

In some embodiments, the bicarbonate containing and/or bicarbonate-producing composition further comprise one or more agents that can increase the pH of the algae growth system. In some embodiments, the composition increases the pH of the algae growth system to at least 6.0, at least 6.5, at least 7.0, at least 7.5, at least 8.0, at least 8.5, at least 9.0, at least 9.5, at least 10.0, at least 10.5, at least 11.0, or more. The optimum pH for any one particular algal growth system may be different based upon the particular genera and/or particular species or strain of algae used in that particular growth system. In some embodiments, after the bicarbonate containing and/or bicarbonate-producing composition has been added to the algae growth system, the pH of the algae growth system may be lowered by addition of an acid. In these embodiments, addition of the bicarbonate containing and/or bicarbonate-producing composition inhibits replication of the algae cells, and after the pH is lowered, the algae cells may deplete the remaining nitrate and/or silica in the culture medium. In certain embodiments, the acid added to the algae growth system may be carbonic acid or a carbonic acid-producing composition. The algae may need $CO_2$ to increase TAG, but bicarbonate can be used to supply the dissolved inorganic carbon (DIC) and arrest replication in the algae.

In some embodiments, the bicarbonate containing and/or bicarbonate-producing composition provides the algae growth system a concentration of bicarbonate of at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 150 mM, at least 200 mM, at least 250 mM, at least 300 mM or more. The optimum concentration of bicarbonate for any one particular algal growth system may be different based upon the particular genera and/or particular species or strain of algae used in that particular growth system.

In some embodiments, the bicarbonate containing and/or bicarbonate-producing composition is added before, at the time, or after nutrient depletion or growth condition changes that inhibit algae replication. In some embodiments, the bicarbonate containing and/or bicarbonate-producing composition is added as close to nutrient depletion as possible. In some embodiments, the bicarbonate containing and/or bicarbonate-producing composition is added into the growth system right before or right after nutrient depletion. In some embodiments, the bicarbonate containing and/or bicarbonate-producing composition is added together with an inorganic nitrogen source and/or an organic nitrogen source after nutrient depletion. In some embodiments, the bicarbonate containing and/or bicarbonate-producing and/or inorganic nitrogen source and/or organic nitrogen source composition is added into the growth system about 1 minute, about 5 minutes, about 10 minutes, about 20 minutes, about half hour, about one hour, about 2 hours, about 3 hours, about 4 hours, about 5 hours, about 6 hours, about 7 hours, about 8 hours, about 9 hours, about 10 hours, about 12 hours, about 24 hours, about 36 hours, about 48 hours, about 60 hours, about 72 hours, about 84 hours, about 96 hours, about 108 hours, about 120 hours, or more before or after nutrient depletion of the growth system. Nutrient depletion time can be determined by running a control algae growth system without adding the composition. The optimum time point in which to add the bicarbonate and/or bicarbonate-producing composition to any one particular algal growth system may be different based upon the particular genera and/or particular species of algae used in that particular growth system.

In some embodiments, the lipid is triacylglycerol (TAG). In some embodiments, the lipid accumulation in the algae growth system is at least 2 times, at least 3 times, at least 4 times, at least 5 times, at least 6 times, at least 7 times, at least 8 times, at least 9 times, at least 10 times, or more of the lipid accumulation in a control algae growth system.

The present invention also provides methods of reducing total time required for producing lipid at a predetermined yield from an algae growth system. In some embodiments, the algae growth system is under light-dark cycling. In some embodiments, said methods comprise adding a composition when algae cells in the growth system are in exponential growth stage, but prior to nutrient depletion of the growth system, wherein the composition comprises bicarbonate, and/or one or more compounds that provide bicarbonate after the composition is added into the algae growth system.

In some embodiments, algae cell growth/replication in the growth system is inhibited before, at the time, or after adding the bicarbonate and/or bicarbonate-producing composition.

In some embodiments, the total time required for producing lipid at a predetermined yield is reduced by at least 10%, at least 20%, at least 30%, at least 40%, at least 50%, at least 60%, at least 70%, at least 80%, at least 90%, or more, compared to the total time required for a control algae growth system.

The present invention also provides bicarbonate and/or bicarbonate-producing compositions for said methods. In some embodiments, the bicarbonate and/or bicarbonate-producing compositions comprise bicarbonate, and/or at least one source that can provide bicarbonate when added into the algae growth system. In some embodiments, the bicarbonate and/or bicarbonate-producing compositions are. in solid form. In some embodiments, the bicarbonate and/or bicarbonate-producing compositions are in liquid form. In some other embodiments, the bicarbonate and/or bicarbonate-producing compositions are in solid-liquid mixture form.

In some embodiments, the source for bicarbonate in the bicarbonate and/or bicarbonate-producing compositions is a bicarbonate salt. For example, the source is sodium bicarbonate, potassium bicarbonate, ammonium bicarbonate, aminoguanidine bicarbonate, choline bicarbonate, magnesium bicarbonate, or combination thereof. In some embodiments, the composition further comprises one or more agents that can increase the pH of the algae growth system.

The present invention also provides methods of increasing lipid accumulation in an algae growth system compared to a control algae growth system. A control algae growth system here is a growth system without or with little bicarbonate (i.e., a system having less than 0.001 mM of bicarbonate, or a system having less than 0.01 mM of bicarbonate) at the beginning and during algae growth. In some embodiments, the methods comprise growing algae in a medium comprising bicarbonate and/or a bicarbonate-producing composition at the starting point. In some embodiments, the concentration of bicarbonate in the medium initially is at least 1 mM, at least 5 mM, at least 10 mM, at least 15 mM, at least 20 mM, at least 30 mM, at least 40 mM, at least 50 mM, at least 60 mM, at least 70 mM, at least 80 mM, at least 90 mM, at least 100 mM, at least 150 mM, at least 200 mM, at least 250 mM, at least 300 mM, or more. In some embodiments, the algae are diatoms. In some further embodiments, the diatom is diatom *Phaeodactylum tricornutum* Pt-1 (Pt-1). In some embodiments, the medium is based on ASP II medium.

As discussed further herein, the inventors of the present invention have discovered that adding a solution containing bicarbonate ions to a growing algal culture prevents further growth but enhances the cell's ability to accumulate triacylglyceride. In some embodiments, to obtain maximum enhancement the bicarbonate must be added before the algal cells have utilized one, more than one, or all the available culture limiting nutrients in the medium and by increasing the pH, for example, by increasing the pH to reach a value greater than pH 10.0. Adding bicarbonate when the medium nitrogen has been utilized will not allow for maximum enhancement. This strongly implies that protein synthesis is required to obtain the desired effect. It is important to realize that this phenomenon is most likely not TAG-specific but the enhancement of product formation may be general. Not only does this invention have major ramifications for industrial production of algal material, but the finding allows "gene activity leading to desired product formation" to be monitored specifically.

DETAILED DESCRIPTION

Figure 1:
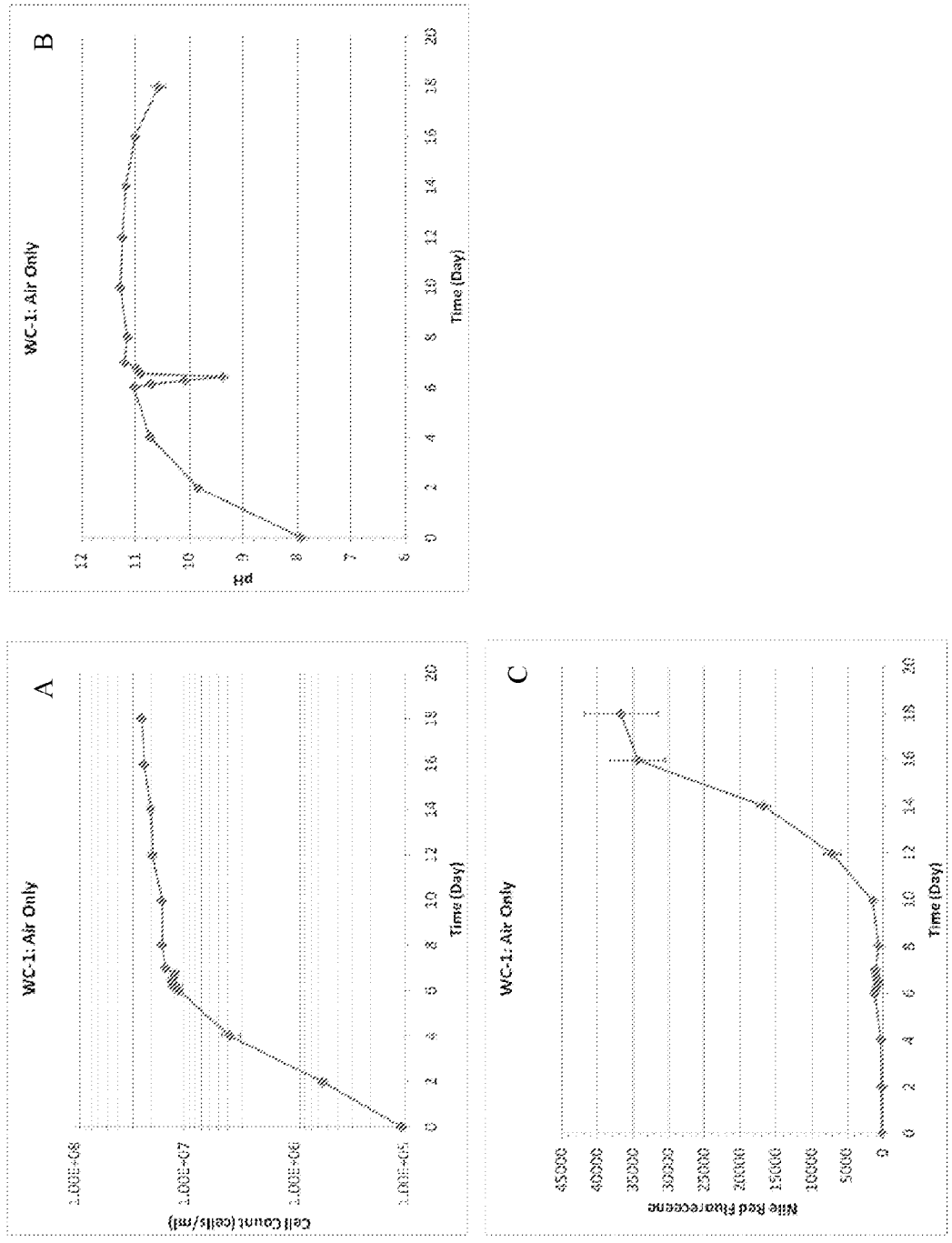
FIG. 1 depicts average cell density, medium pH, and Nile Red Fluorescence of *Scenedesmus* WC-1 grown on 14:10 L:D cycle in unbuffered Bold's Basal Medium, ambient air aeration. Error is standard deviation. n=3

Lipid derived biofuel is defined as fatty acid methyl esters (FAME) derived from triacylglycerol (TAG) which can be synthesized in plant, animal, or microalgae biomass. FAMEs offer increased energy yield, over input requirements, as compared to biologically derived ethanol and can be used directly in jet or diesel engines [1, 2]. However, FAME precursor TAG availability will limit the use of this fuel to mediate global transportation needs unless non-food crop land acreage and hypersaline, brackish, high alkalinity, or wastewater can be used to produce the fuel. Due to the fast growth rate and physiological diversity microalgae exhibit [3], they are well suited to be used in intelligently designed growth systems that bypass food crop land, facilitate higher mass transfer, and potentially decrease microbial contamination [4].

Historically, a major goal of the Aquatic Species Program, which initially evaluated algae's potential for biofuel production, was to identify a "lipid trigger" [5]. This would be a set of environmental parameters or target molecule(s) that would promote algal synthesis of TAG. No trigger was identified, however nitrogen depletion has been shown to cause cellular lipid accumulation, albeit some strains can take many days to accumulate the TAG [4, 6]. Additionally, we have observed delayed cell growth/replication by inhibiting the tricarboxylic acid cycle with monofluoroacetic acid [7]), inducing cellular TAG accumulation, and similarly we have observed pH induced TAG accumulation [8]. Recently, these results have been expanded proving that pH induced TAG accumulation and nitrate depletion causing TAG accumulation are independent stress mechanisms. An advantageous interplay between pH and nitrate was identified which showed both an increase in TAG per cell and a much shortened culture time to realize nitrate depletion generated TAG accumulation [4]. However, both of these pH studies were conducted with 24 hr light conditions which will inherently limit dark cycle respiration.

The present invention discloses an extension of pH studies aimed at understanding the cellular metabolic responses during pH induced, or pH induced combined with nutrient depletion (e.g., nitrate or silica depletion), TAG accumulation and the hypothesis of the existence of a TAG accumulation inducing trigger. In some embodiments, inventors of the present invention detail a loss of pH induced TAG accumulation when cultures are shifted from 24 hr light conditions to 14:10 light-dark cycling, and by following the inventors' hypotheses that cell growth/replication inhibition leads to TAG accumulation and high pH coupled with nutrient depletion causes increased TAG accumulation, with decreased culture time to reach high TAG levels, a bicarbonate trigger was found. This trigger changes a culture from high biomass with little TAG to a high TAG accumulation state. In other words, it stops cell growth/replication but maintains photosynthesis forcing the algae to fix carbon as lipid.

Without wishing to be bound by any theory, any composition (e.g., bicarbonate) or any growth factor change (temperature, pH, light, etc) that can influence the ability of an algae cell to complete a growth cycle (wherein energy is needed for cell division) will cause TAG accumulation in an algae growth system, if adding said composition into the system or making said growth factor change to the system is not completely toxic and/or does not result in cell death. Bicarbonate is such a composition.

DEFINITION

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, the term "derived from" refers to the origin or source, and may include naturally occurring, recombinant, unpurified, or purified molecules.

The terms "algae" or "algal" are used synonymously herein and refer to the common (non-taxonomic) name for a large and diverse group of a relatively simple type of thallophytic plant which is never differentiated into distinct organs such as root, stem and leaves. They contain chlorophyll and are photosynthetic. Algae display a stunning variety of shapes, sizes, and colors and range in form from unicellular to multicellular, the latter including plants many meters in length, such as what is commonly known as seaweed. Examples of algae include but are not limited to blue green algae (cyanobacteria, Cyanophycae), red algae or Rhodophyta (e.g., *Porphyra, Iridaea*); dinoflagellates (e.g., *Peridinium, Ceratium*); diatoms (e.g., *Thalassiosira*); golden-brown algae (e.g., *Vaucheria*); brown algae or Phaeophyta (e.g., *Laminaria, Postelsia, Macrocystis, Nereocystis, Fucus*); and green algae or Chlorophyta (*Nannochloropsis, Hydrodictyon, Spirogyra, Zygnema, Closterium, Mougeotia, Micrasterias, Cosmarium, Desmidium, Oedogonium, Coleochaeie, Cladophora, Codium, Chara, Ulva, Bryopsis, Ulothrix*). For a more comprehensive description of algae, see, for example, Lee, R. E. (2008) Phycology, Cambridge University Press 547 pages; Barsanti, et al. (2005) Algae: Anatomy, Biochemistry, and Biotechnology, First Edition, ISBN-10: 0849314674, CRC Press, 320 pages; and Brodie et al. (editors) (2007) Unraveling the algae: the past, present, and future of algal systemics, First Edition, CRC Press, 402 pages, each of which is herein incorporated by reference in their entireties.

As used herein, the term "agent", as used herein, means a biological or chemical compound such as a simple or complex organic or inorganic molecule, a peptide, a protein or an oligonucleotide that modulates the function of a nucleic acid or polypeptide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

As used herein, the term "bicarbonate" or "hydrogencarbonate" refers to an intermediate form in the deprotonation of carbonic acid. Its chemical formula is $HCO_3$, and as used herein is synonymous with $HCO_3$.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transgenic" refers to cells, cell cultures, organisms (e.g., plants), and progeny which have received a foreign or modified gene by one of the various methods of transformation, wherein the foreign or modified gene is from the same or different species than the species of the organism receiving the foreign or modified gene.

As used herein, unless otherwise specified, the term "carbohydrate" refers to a compound of carbon, hydrogen, and oxygen that contains an aldehyde or ketone group in combination with at least two hydroxyl groups. The carbohydrates of the present invention can also be optionally substituted or deoxygenated at one or more positions. Carbohydrates thus include substituted and unsubstituted monosaccharides, disaccharides, oligosaccharides, and polysaccharides. The saccharide can be an aldose or ketose, and may comprise 3, 4, 5, 6, or 7 carbons. In one embodiment they are monosaccharides. In another embodiment they can be pyranose and furanose sugars. They can be optionally deoxygenated at any corresponding C-position, and/or substituted with one or more moieties such as hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, thioester, thioether, oxime, hydrazine, carbamate. These saccharide units can be arranged in any order and the linkage between two saccharide units can occur in any of approximately ten different ways. As a result, the number of different possible stereoisomeric oligosaccharide chains is enormous. In one embodiment, said carbohydrates are selected from the group consisting of monosaccharides, disaccharides, oligosaccharides, polysaccharides, and a combination thereof.

As used herein, the term "neutralize", "neutralizing", and "neutralization" refers to a chemical reaction in aqueous solutions, wherein an acid and a base react to form water and a salt, and wherein the pH of the solution is brought closer to 7.

As used herein, the term "aerobic conditions" refers to conditions where sufficient oxygen, is provided, and anaerobic respiration in a microorganism growing under such conditions is prohibited.

As used herein, the term "substantially aerobic conditions" refers to conditions wherein the supply of oxygen is limited, but the cellular respiration in an organism is dominantly aerobic respiration.

As used herein, the term "biofuel" (also called bioenergy) is defined as solid, liquid or gaseous fuel derived from relatively recently dead or dying biological material and is distinguished from fossil fuels, which are derived from long dead biological material. It can be produced from any biological carbon source theoretically. Biofuels can be classified into first generation biofuels (which are made from sugar, starch, vegetable oil, and animal fats, including but not limited to vegetable oil, biodiesel, bioalcohols, bioethers, biogas, syngas and solid biofuels), second generation biofuels (which are produced from biomass of non food crops, also called cellulosic biofuels, including but not limited to, biohydrogen, biomethanol, DMF, Bio-DME, Fischer-Tropsch diesel, biohydrogen diesel, mixed alcohols and wood diesel), and third generation biofuels (also called algae fuels, which are made from algae).

The term "biofuel precursor" refers to an organic molecule in which all carbon contained within is derived from biomass and is biochemically converted. It can be further converted either chemically or biochemically, into a biofuel. For example, a biofuel precursor includes, but is not limited to, e.g. isobutanol, isopropanol, propanol, 2-butanol, butanol, pentanol, 2-pentanol, 3-pentanol, 3-methyl-1-butanol, 2-methyl-1-butanol, 3-methyl-2-butanol, and lipid.

As used herein, the term "biodiesel" refers to a vegetable oil or animal fat-based diesel fuel consisting of long chain alkyl (e.g., methyl, propyl or ethyl) esters. It can be made by chemically reacting lipids with one or more types of alcohol in a transesterification reaction. Chemically it comprises a mix of mono-alkyl esters of long chain fatty acids. Alcohols that can be used to produce biodiesel include, but are not limited to, methanol, ethanol, propanol, isopropanol, butanol, isobutanol, and 2-ethoxyethanol. Acidic or alkaline catalyst can be applied to facilitate esterification of fatty acids. Glycerol is produced as a by-product in such reactions.

As used herein, the phrase "fatty acids" refers to long-chained molecules having a methyl group at one end and a carboxylic acid group at the other end.

As used herein, the term "fermentation" or "fermentation process" refers a process in which a biocatalyst is cultivated in a culture medium containing raw materials, such as feedstock and nutrients, wherein the biocatalyst converts raw materials, such as a feedstock, into products.

As used herein, the term "carbon source" generally refers to a substance suitable to be used as a source of carbon for prokaryotic or eukaryotic cell growth. Carbon sources include, but are not limited to, carbon dioxide, bicarbonate, carbonate, biomass hydrolysates, carbohydrates (e.g., starch, sucrose, polysaccharides, and monosaccharides), cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis.

As used herein, the term "biomass" refers to biological material derived from living, or recently living organisms, e.g., stems, leaves, and starch-containing portions of green plants, or wood, waste, forest residues (dead trees, branches and tree stumps), yard clippings, wood chips, or materials derived from algae or animals, and is mainly comprised of starch, lignin, pectin, cellulose, hemicellulose, and/or pectin. Biomass may also include biodegradable wastes that can be burnt as fuel. It excludes organic material such as fossil fuel which has been transformed by geological processes into substances such as coal or petroleum. Biomass can be decomposed by either chemical or enzymatic treatment to the monomeric sugars and phenols of which it is composed (Wyman, C. E. 2003 Biotechnological Progress 19:254-62). This resulting material, called biomass hydrolysate, is neutralized and treated to remove trace amounts of organic material that may adversely affect the biocatalyst, and is then used as a feedstock for fermentations using a biocatalyst.

As used herein, the term "nutrient" is defined as a chemical compound that is used by a biocatalyst to grow and survive. Nutrients can be organic compounds such as carbohydrates and amino acids or inorganic compound such as metal or mineral salts.

As used herein, the term "recombinant microorganism" and "recombinant host cell" are used interchangeably and refer to microorganisms that have been genetically modified to express or over-express endogenous polynucleotides, or to express heterologous polynucleotides, such as those included in a vector, or which have a reduction in expression of an endogenous gene. The polynucleotide generally encodes a target enzyme involved in a metabolic pathway for producing a desired metabolite. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

As used herein, the term "fermentation" refers to a method to produce biofuel and other products where biomass (pretreated or unpretreated) was fermented by microorganisms (e.g., bacteria, cyanobacteria, yeast, fungi or algae).

Algae

Algae are a large and diverse group of simple, typically autotrophic organisms, ranging from unicellular to multicellular forms, such as the giant kelps that grow to 65 meters in length. The US Algal Collection is represented by almost 300,000 accessioned and inventoried herbarium specimens.

Non-limiting examples of algae include, Archaeplastida (e.g., *Chlorophyta* (Green algae), Rhodophyta (Red algae), Glaucophyta), *Rhizaria, Excavata* (e.g., Chlorarachniophytes, Euglenids), and Chromista, Alveolata (e.g., Heterokonts (e.g., Bacillariophyceae (Diatoms), Axodine, *Bolidomonas*, Eustigmatophyceae, Phaeophyceae (Brown algae), Chrysophyceae (Golden algae), Raphidophyceae, Synurophyceae, Xanthophyceae (Yellow-green algae)), Cryptophyta, Dinoflagellates, and Haptophyta).

All true algae have a nucleus enclosed within a membrane and plastids bound in one or more membranes. Algae constitute a paraphyletic and polyphyletic group, as they do not include all the descendants of the last universal ancestor nor do they all descend from a common algal ancestor, although their plastids seem to have a single origin.

Algae lack the various structures that characterize land plants, such as phyllids (leaves) and rhizoids in nonvascular plants, or leaves, roots, and other organs that are found in tracheophytes (vascular plants). Many are photoautotrophic, although some groups contain members that are mixotrophic, deriving energy both from photosynthesis and uptake of organic carbon either by osmotrophy, myzotrophy, or phagotrophy. Some unicellular species rely entirely on external energy sources and have limited or no photosynthetic apparatus.

Nearly all algae have photosynthetic machinery ultimately derived from the Cyanobacteria, and so produce oxygen as a by-product of photosynthesis, unlike other photosynthetic bacteria such as purple and green sulfur bacteria.

Rhodophyta, Chlorophyta and Heterokontophyta, the three main algal Phyla, have life-cycles which show tremendous variation with considerable complexity. In general there is an asexual phase where the seaweed's cells are diploid, a sexual phase where the cells are haploid followed by fusion of the male and female gametes. Asexual reproduction is advantageous in that it permits efficient population increases, but less variation is possible. Sexual reproduction allows more variation, but is more costly. Often there is no strict alternation between the sporophyte and also because there is often an asexual phase, which could include the fragmentation of the thallus.

Diatoms are eukaryotic, unicellular, algae that make a siliceous cell wall. They constitute the largest population of algae in the oceans and fix carbon for 40% of marine productivity. Most diatoms are unicellular, although they can exist as colonies in the shape of filaments or ribbons (e.g. *Fragillaria*), fans (e.g. Meridian), zigzags (e.g. *Tabellaria*), or stellate colonies (e.g. *Asterionella*). A characteristic feature of diatom cells is that they are encased within a unique cell wall made of silica (hydrated silicon dioxide) called a frustule. These frustules show a wide diversity in form, but usually consist of two asymmetrical sides with a split between them, hence the group name. There are more than 200 genera of living diatoms, and it is estimated that there are approximately 100,000 extant species [30-32]. Diatoms belong to a large group called the heterokonts, including both autotrophs (e.g. golden algae, kelp) and heterotrophs (e.g. water moulds). Their yellowish-brown chloroplasts are typical of heterokonts, with four membranes and containing pigments such as the carotenoid fucoxanthin. Individuals usually lack flagella, but they are present in gametes and have the usual heterokont structure, except they lack the hairs (mastigonemes) characteristic in other groups. Some species actively regulate their buoyancy with intracellular lipids to counter sinking. The entire genomes of the centric diatom, *Thalassiosira pseudonana* (32.4 Mb) [33] and the pennate diatom, *Phaeodactylum tricornutum* (27.4 Mb) [34], have been sequenced. Detailed study of diatoms can be found in Lewin et al., 1963 (Annual review of microbiology, *Diatoms*, Vol. 17: 373-414) and Werner, 1977 (The Biology of Diatoms, ISBN 0520034007, 9780520034006), each of which is incorporated herein by reference in its entirety.

Algae biology, strains, technology, mechanism and non-limited examples of commercialization of algal biofuel production are described in Singh et al. 2010a, 2010b, 2010c, Sims et al., 2010, Demirbas, et al., Demirbas et al., Khattar et al., Miller et al., Chen et al. (Ref. Nos 21-28), *A Look Back at the U.S. Department of Energy's Aquatic Species Program: Biodiesel from Algae* (National Renewable Energy Laboratory, Close-Out Report, 1998), and *National Algal biofuels Technology Roadmap* (U.S. Department of Energy, May 2010), each of which is incorporated herein by reference in its entirety for all purposes.

To produce biofuel, algae can be cultivated in photobioreactors, closed loop systems, or open ponds, under aerobic conditions, or substantially aerobic conditions. In a photobioreactor (PBR), nutrient-laden water is pumped through plastic tubes that are exposed to light. A PBR is a bioreactor which incorporates some type of light source. Virtually any translucent, closed container can be called a PBR. PBRs are designed to prevent the growth of unwanted species. A PBR can be operated in "batch mode", but it is also possible to introduce a continuous stream of sterilized water containing nutrients, air, and carbon dioxide. As the algae grows, excess culture overflows and is harvested. Light source can be artificial light, solar light, or mixture thereof. PBR temperature can be controlled by placing it in a constant temperature room or bath. Large scale outdoor PBRs with temperature control are also commercially available. Non-limiting exemplary PBRs include, flat-panel PBRs, tubular PBRs (horizontal or vertical), bubble column PBRs, air lift PBRs, stirred tank PBRs, immobilized PBRs, vertical-column PBRs, and those described in Lehr and Posten (Closed photo-bioreactors as tools for biofuel production, *Current Opinion in Biotechnology*, 2009, 20:280:285) and U.S. Pat. Nos. 5,958,761, 7,449, 313, 5,981,271, 6,432,698, 7,514,247, 6,571,735, 4,743,545, 6,008,028, 6,174,720, 7,001,519, 7,229,785, 7,004,109, 5,614,097, 5,569,634, 6,986,323, and 6,923,914, each of which is hereby incorporated by reference in its entirety for all purposes. In a closed system (not exposed to open air), algae for biofuel production can be grown in large quantities, and contamination by other organisms in the air is prevented. Some algae production systems can be built next to power plants use effluent of $CO_2$ to reduce pollution. In such systems, control over the environment is much better than in the open ponds. Open-pond systems include natural waters and artificial ponds or containers. The most commonly used systems include shallow big ponds, tanks, circular ponds and raceway ponds. One major advantage of open ponds is that they are easier and cheaper to construct and operate than most closed systems.

Lipid

Lipids are a broad group of naturally occurring molecules which includes fats, waxes, sterols, fat-soluble vitamins (such as vitamins A, D, E and K), monoglycerides, diglycerides, phospholipids, and others. Although the term lipid is sometimes used as a synonym for fats, fats are a subgroup of lipids called triglycerides. Lipids also encompass molecules such as fatty acids and their derivatives (including tri-, di-, and monoglycerides and phospholipids), as well as other sterol-containing metabolites such as cholesterol. Although humans and other mammals use various biosynthetic pathways to both break down and synthesize lipids, some essential lipids cannot be made this way and must be obtained from the diet. Non-limiting examples of lipids include, fatty acyls, glyercolipids, glycerophospholipids, sphingolipids, sterol lipids, prenol lipids, polyketides, and saccharolipids.

Triacylglycerol (TAG)

Triacylglycerol (a.k.a. Triglyceride, TAG or triacylglyceride) is an ester derived from glycerol and fatty acids. It is the main constituent of vegetable oil and animal fats.

Triglycerides are formed by combining glycerol with three molecules of fatty acid. The glycerol molecule has three hydroxyl (HO—) groups. Each fatty acid has a carboxyl group (HOOC—). In triglycerides, the hydroxyl groups of the glycerol join the carboxyl groups of the fatty acid to form ester bonds:

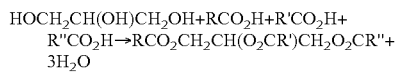

The three fatty acids ($RCO_2H$, $R'CO_2H$, $R''CO_2H$ in the above equation) are usually different, but many kinds of triglycerides are known. The chain lengths of the fatty acids in naturally occurring triglycerides vary in lengths, but most contain 16-, 18-, and 20-carbon atoms. Natural fatty acids found in plants and animals are typically composed only of even numbers of carbon atoms, reflecting the pathway for their biosynthesis from the two-carbon building block acetyl CoA. Bacteria, however, possess the ability to synthesize odd- and branched-chain fatty acids. As a result, ruminant animal fat contains odd-numbered fatty acids, such as 15, due to the action of bacteria in the rumen. Many fatty acids are unsaturated, some are polyunsaturated, e.g., those derived from linoleic acid.

Figure 6:
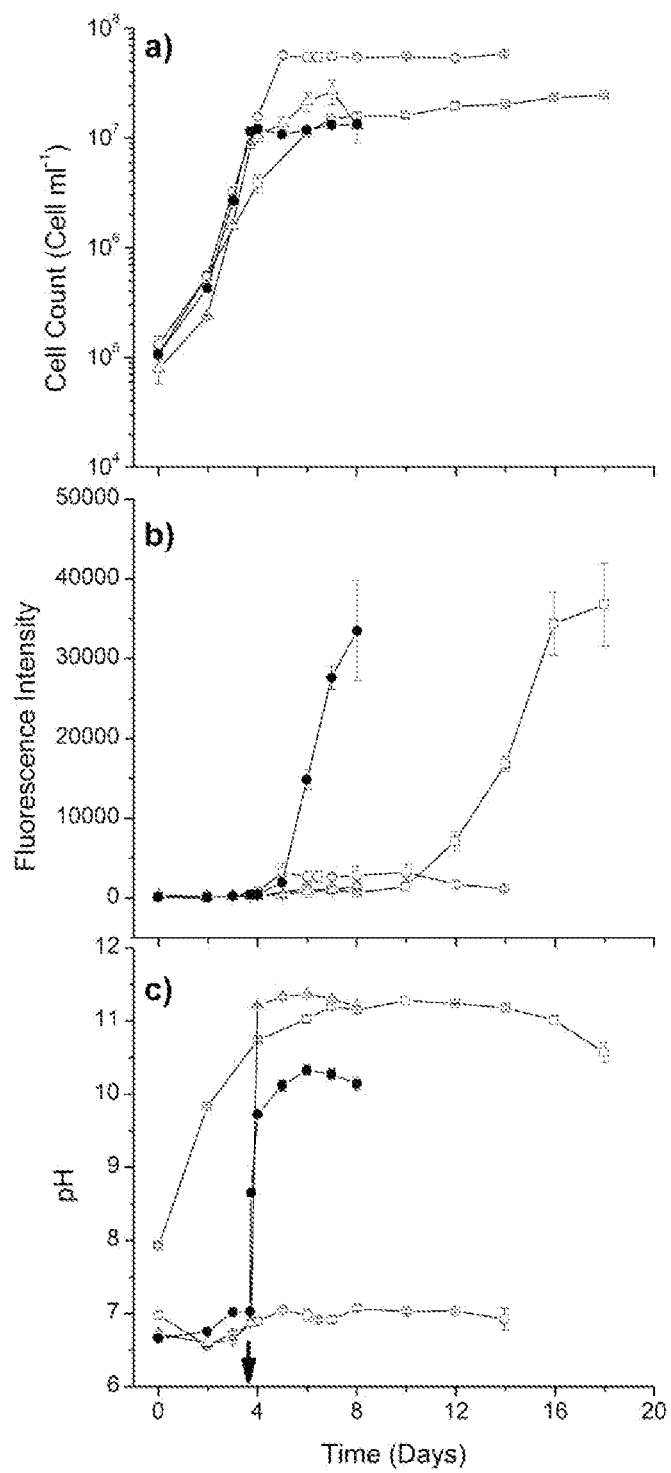
FIG. 6 depicts average and standard deviation of cellular growth (a), total Nile Red fluorescence intensity (b), and culture pH (c) of *Scenedesmus* WC-1 aerated with ambient air (□), 5% $CO_2$ in air (○), and 5% $CO_2$ in air that is changed to ambient air near nitrate depletion, both with (●) and without (Δ) a 50 mM bicarbonate addition. Arrow indicates time of bicarbonate addition. Growth was maintained in unbuffered Bold's basal medium illuminated with a 14:10 L:D cycle. n=3

Algae produce triacylglycerols from fatty acids. Major pathways for fatty acids and TAG synthesis in algae are shown in FIG. 6. Under favorable growth conditions, newly photoassimilated carbon is incorporated primarily into proteins. Thus, lipid levels are generally low under log phase growth conditions. Moreover, lipids made during daylight are used as energy sources during dark periods. It has long been recognized that lipid accumulation is an adaptive response to stress for algae. Under biotic and abiotic stresses, such as low light or temperature, high light intensity or salinity, low nutrients, or fluctuations in pH, more carbon is incorporated into lipids and carbohydrates and less is incorporated into proteins. The profile of the fatty acid composition of the lipids also changes under stress. Algae must cope with fluctuations in conditions in order to survive. Lipids serve as carbon and energy storage for "hard times". It has recently been suggested that lipid accumulation may even play a protective role against excess sunlight by serving as an electron sink when excess electrons accumulate from the photosynthetic electron transport chain under photo-oxidative stress (Hu et al. (2008). Microalgal triacylglycerols as feedstocks for biofuel production: Perspectives and advances. Plant Journal. 54(4), 621-639.). The better the response to environmental stresses, the better the survival of the species, so genes in stress response pathways are often positively selected. For algae grown commercially, direct competition with conspecifics (as more and more cells are packed into a limited volume), and predation by protists are additional stresses.

Many algae are photosynthetic organisms capable of harvesting solar energy and converting $CO_2$ and water to $O_2$ and organic macromolecules such as carbohydrates and lipids. Under stress conditions such as high light or nutrient starvation, some microalgae accumulate lipids such as triacylglycerols (TAG) as their main carbon storage compounds. Certain microalgal species also naturally accumulate large amounts of TAG (30-60% of dry weight), and exhibit photosynthetic efficiency and lipid production at least an order of magnitude greater than terrestrial crop plants (Hu et al., 2008). Cyanobacteria and macroalgae, as a general rule, accumulate mostly carbohydrates, with lipid accumulation in macroalgae typically being less than 5% of total dry weight (McDermid et al. (2003). Nutritional composition of edible Hawaiian seaweeds. Journal of Applied Phycology, 15(6), 513-524.), although concentrations approaching 20% lipid have been reported in some species (Chu et al. (2003). Fatty Acid Composition of Some Malaysian Seaweeds. Malaysian Journal of Science. 22(2), 21-27; Mcdermid et al. 2003). Lipids and carbohydrates, along with biologically produced hydrogen and alcohols, are all potential biofuels or biofuel precursors.

Knowing how and when carbon is partitioned in a cell into lipids and/or carbohydrates could be very useful for biofuels strain development and designing cultivation strategies. Understanding carbon partitioning will require extensive knowledge of metabolic pathways. Metabolic networks have been reconstructed in various microbes from genomic and transcriptomic data, pathway analysis, and predictive modeling (Vemuri, G. N. A. A. Aristidou. (2005). Metabolic engineering in the -omics era: Elucidating and modulating regulatory networks. Microbiology and Molecular Biology Reviews. 69(2), 197-216.). Research has also been done in plant systems to understand carbon flux in biosynthetic and degradative pathways (Lytovchenko et al., 2007; Schwender et al., 2004; Allen et al., 2009; Sweetlove and Fernie, 2005; Libourel and Shachar-Hill, 2008). However, carbon partitioning in algae is less understood and research on how algal cells control the flux and partitioning of photosynthetically fixed carbon into various groups of major macromolecules (i.e., carbohydrates, proteins, and lipids) is critically needed.

Further, a link between starch and lipid metabolism has been established. Starch is a common carbon and energy storage compound in plants and algae, and shares the same precursors with the storage lipid TAG. It is, therefore, possible that TAG and starch could be inter-convertible, a potentially important implication for biofuel production. More recently, studies in higher plants showed that when starch synthesis was impaired or inhibited, plant embryos or seeds accumulated 40% less oil (Periappuram et al., 2000; Vigeolas et al., 2004). While these results provide an indication that starch synthesis is linked to lipid synthesis, the nature of the interaction is unknown.

Some algae, naturally or under stress conditions, accumulate significant quantities of neutral storage lipids such as triacylglycerols (TAG), which are important potential fuel precursors. The major pathway for the formation of TAG in plants first involves de novo fatty acid synthesis in the stroma of plastids. The synthesis of cellular and organelle membranes, as well as of neutral storage lipids such as TAG, uses 16 or 18 carbon fatty acids as precursors. TAG is formed by incorporation of the fatty acid into a glycerol backbone via three sequential acyl transfers (from acyl CoA) in the endoplasmic reticulum (ER).

TAG biosynthesis in algae has been proposed to occur via the above Kennedy pathway described in plants. Fatty acids produced in the chloroplast are sequentially transferred from CoA to positions 1 and 2 of glycerol-3-phosphate, resulting in the formation of the central metabolite phosphatidic acid (PA). Dephosphorylation of PA catalyzed by a specific phosphatase releases diacylglycerol (DAG). Since diglycerides are usually present in high amounts in rapidly growing cultures, it may be of interest to research these TAG intermediates. In the final step of TAG synthesis, a third fatty acid is transferred to the vacant position 3 of DAG by diacylglycerol acyltransferase, an enzyme that is unique to TAG biosynthesis. The acyltransferases involved in TAG synthesis may exhibit preferences for specific acyl CoA molecules, and thus may play an important role in determining the final acyl composition of TAG (Hu et al., 2008). Alternative pathways to convert membrane lipids and/or carbohydrates to TAG have recently been demonstrated in bacteria, plants and yeast in an acyl CoA-independent way (Arabolaza et al., 2008; Dahlqvist et al., 2000; Stahl et al., 2004). Such pathways have not yet been studied in algae. Moreover, PA and DAG can also be used directly as substrates for synthesis of polar lipids, such as phosphatidylcholine (PC) and galactolipids. These pathways are worth investigating when developing strains for improved lipid production.

The regulation of the synthesis of fatty acids and TAG in algae is relatively poorly understood. This lack of understanding may contribute to why the lipid yields obtained from algal mass culture efforts fall short of the high values (50 to 60%) observed in the laboratory. Understanding lipid regulation can help to maximize scenarios for lipid production and strain improvement.

Lipids in algae can be extracted using different procedures. Non-limiting examples of lipids extraction are described in King et al. (Supercritical Fluid Extraction: Present Status and Prospects, 2002, *Grasa Asceites,* 53, 8-21), Folch et al. (A simple method for the isolation and purification of total lipids from animal tissues, 1957, *J. Biol. Chem.,* 226, 497-509), Bligh and Dyer (A rapid method of total lipid extraction and purification. 1959, *Can. J. Biochem. Physiol.,* 37, 911-917), Hara et al. (Lipid extraction of tissues with a low toxicity solvent. 1978, *Anal. Biochem.,* 90, 420-426), Lin et al. (Ethyl acetate/ethyl alcohol mixtures as an alternative to Folch reagent for extracting animal lipids. 2004, J. Agric. Food Chem., 52, 4984-4986), Whiteley et al. (Lipid peroxidation in liver tissue specimens stored at subzero temperatures. 1992, Cryo-Letters, 13, 83-86). In another example, lipid can be extracted by methods similar to the FRIOLEX® (Westfalia Separator Industry GmbH, Germany) process is used to extract the biological oils produced by the microorganisms. FRIOLEX® is a water-based physical oil extraction process, whereby raw material containing oil can be used directly for extracting oil without using any conventional solvent extraction methods. In this process, a water-soluble organic solvent can be used as a process aid and the oil is separated from the raw material broth by density separation using gravity or centrifugal forces.

After the lipids have been extracted, the lipids can be recovered or separated from non-lipid components by any suitable means known in the art. For example, low-cost physical and/or mechanical techniques are used to separate the lipid-containing compositions from non-lipid compositions. If multiple phases or fractions are created by the extraction method used to extract the lipids, where one or more phases or fractions contain lipids, a method for recovering the lipid-containing phases or fractions can involve physically removing the lipid-containing phases or fractions from the non-lipid phases or fractions, or vice versa. In some embodiments of the present invention, a FRIOLEX® type method is used to extract the lipids produced by the microorganisms and the lipid-rich light phase is then physically separated from the protein-rich heavy phase (such as by skimming off the lipid-rich phase that is on top of the protein-rich heavy phase after density separation).

Once the lipids are produced in accordance with the present invention, various methods known in the art can be used to transform the biological oils into esters of fatty acids for use as biodiesel, jet biofuel, or as ingredients for food or pharmaceutical products. In some embodiments of the present invention, the production of esters of fatty acids comprises transesterifying the biological oils produced by the microorganism. In some embodiments of the present invention, the extraction of the lipids from the microorganisms and the transesterification of the lipids can be performed simultaneously, in a one step method. For example, the culture containing the algae can be exposed to conditions or treatments (or a combination of conditions or treatments) that promote both extraction of the lipids and the transesterification of the lipids. Such conditions or treatments could include, but are not limited to, pH, temperature, pressure, the presence of solvents, the presence of water, the presence of catalysts or enzymes, the presence of detergents, and physical/mechanical forces. Two sets of conditions or treatments could be combined to produce a one step method of extracting and transesterifying the lipids, where one set of conditions or treatments favorably promotes extraction of the lipids and the other set of conditions or treatments favorably promotes transesterification of the lipids, so long as the two sets of conditions or treatments can be combined without causing significant reduction in the efficiency of either the extraction or the transesterification of the lipids. In some embodiments of the present invention, hydrolysis and transesterification can be performed directly of whole-cell biomass. In other embodiments of the present invention, the extraction of the lipids is performed as a step that is separate from the step of transesterification of the lipids. In one embodiment, such transesterification reactions are performed using acid or base catalysts. In some embodiments of the present invention, methods for transesterifying the biological lipids into esters of fatty acids for use as biodiesel or as ingredients for food or pharmaceutical products involve reacting the biological oils containing triglycerides in the presence of an alcohol and a base to produce esters of the fatty acid residues from the triglycerides.

Methods and Compositions

The inventors of the present invention previously observed how elevated pH can cause TAG accumulation in an algae growth system, and how it can be combined with nutrient depletion to induce lipid accumulation, wherein the system is under constant light condition (24 hours light/day). However, in an algae growth system under light-dark cycling condition, pH induced lipid accumulation does not happen when the algae are in exponential growth. To solve this problem, the inventors of the present invention provide methods and compositions to induce lipid accumulation in an algae growth system, wherein the algae growth system is under light-dark cycling conditions or under continuous dark conditions. The present methods and composition also allows inducing lipid accumulation when the algae are in their exponential growth stage.

The light-dark cycling condition can be selected depending algae strains, light source availabilities, and other factors. In some embodiments, the light-dark cycling has a fixed light-dark ratio. For example, the light-dark ratio can be about 1:23, about 2:22, about 3:21, about 4:20, about 5:19, about 6:18, about 7:17, about 8:16, about 9:15, about 10:14, about 11:13, about 12:12, about 13:11, about 14:10, about 15:9, about 16:8, about 17:7, about 18:6, about 19:5, about 20:4, about 21:3, about 22:2, or about 23:1. In some other embodiments, the light-dark cycling has a dynamic ratio. For example, the light course can be complete natural light, which has a varied, dynamic light-dark ratio day by day.

In some embodiments, the methods of inducing TAG accumulation in the algae growth system comprise adding a composition to algae cells that are grown with little or no light. Such algae cells with little or no light may grow under heterotrophic conditions. These algae can assimilate organic substances to cover variable part of their carbon and energy requirements. To cover their entire energy requirements and be able to grow in complete darkness, the organic substances are respired in mitochondria with oxygen as an electron acceptor, a process similar to respiration in animal cells. Some algae may also use a slightly modified process to respire acetate called the glyoxylate pathway.

Organic substances that may be respired by algae cells in heterotrophic growth conditions include glucose, acetate, glycerol, TCA cycle intermediates (e.g., citric acid) and a number of amino acids. Glucose, acetate and glycerol may play a role as substrates in industrial productions. These compounds are small molecules and are generally available to algae cells as metabolites. Some algae, such as those in the classes Dinophyceans and Prymnesiophyceans, are able to engulf large molecules and particles in a process called pinocytosis or fagocytosis. These algae may be able to grow under heterotrophic conditions by metabolizing larger molecules such as proteins.

In some embodiments, the methods of inducing TAG accumulation in the algae growth system comprise adding a composition to algae cells that are grown under continuous light. In other embodiments, the algae cells are grown under continuous dark conditions or under light-dark cycling conditions but not under continuous light conditions.

In some embodiments, the methods of inducing TAG accumulation in the algae growth system comprise adding a composition when algae cells in the growth system are in exponential growth stage, but prior to nutrient depletion of the growth system. In some embodiments, algae cell growth/replication in the growth system is inhibited before, at the time, or after adding the composition. In some embodiments, the inhibiting step can happen after the algae in the system enter exponential growth stage, but prior to nutrient depletion of the growth system.

In some embodiments, the methods of inducing TAG accumulation in the algae growth system comprise adding a composition when algae cells in the growth system are in stationary growth stage after nutrient depletion of the growth system. The composition in these embodiments comprises an inorganic nitrogen source and/or an organic nitrogen source with bicarbonate and/or one or more compounds that provide bicarbonate after the composition is added into the algae growth system. As used herein, an "inorganic nitrogen source" is a compound or group of compounds that lack carbon and that provide nitrogen to the algae cells in a form that supports cellular replication. As used herein, an "organic nitrogen source" is a compound or group of compounds that contain carbon and that provide nitrogen to the algae cells in a form that supports cellular replication. Non-limiting examples of inorganic nitrogen sources are ammonium ($NH_4^+$) containing compounds, nitrite ($NO_2^-$) containing compounds, and nitrate ($NO_3^-$) containing compounds, and non-limiting examples of organic nitrogen sources are urea, hypoxanthine, guanine, ornithine, glucosamine, and lysine. See Berman et al. (1999), Algal growth on organic compounds as nitrogen sources. Journal of Plankton Research 21(8):1423-1437.

To determine the exponential growth stage, and/or determine the time point at which nutrient depletion happens in a real growth system, a preliminary trial growth system can be applied. The preliminary trial growth system can have a scaled-up, the same, or a scaled-down size compared to the real growth system. One skilled in the art would be able to monitor the growth curve of algae and measure nutrient availability of the growth system in the preliminary trial growth system to decide when to inhibit algae cell growth/replication and when to add compositions of the present invention by estimation and prediction based on analysis on the preliminary trial growth system. Alternatively, one skilled in the art can continue monitoring and measuring a real growth system to determine when to inhibit and when to add the composition in. Concentration of a certain nutrient element (e.g., nitrate, sulfate, phosphate, iron, or silica) can be measured and used as an indicator to decide the time point when nutrient depletion happens in the growth system. Nitrate depletion in Bolds Basal Medium can be measured by ion chromatography, and nitrate depletion in ASP II Medium can be measured using a colorimetric assay based on the reaction of Czechrome NAS reagent (Polysciences Inc., Warrington, Pa.). Measurement of phosphate, sulfate, and nitrate in the culture medium is described by Gardner, et al. (2010), Medium pH and nitrate concentration effects on accumulation of triacylglycerol in two members of the *Chlorophyta*, Journal of Applied Phycology 1-12, DOI: 10.1007/s10811-010-9633-4). Silica depletion may be measured by the method of McLaren et al. (1985), Determination of trace metals in seawater by inductively coupled plasma mass spectrometry with preconcentration on silica-immobilized 8-hydroxyquinoline," Anal. Chem. 57 (14), 2907-2911 DOI: 10.1021/ac00291a037.

The inhibiting step can utilize one or more methods that can inhibit algae cell growth. As used herein, the phrase "inhibiting algae growth" or "inhibits algae cell growth" refers to reducing, or completely preventing algae cell growth in an algae growth system. As a result, the algae cell growth as measured by growth rate is reduced by at least 5%, at least 10%, at least 20%, at least 30%, at least 40%, at least 50%, at least 60%, at least 70%, at least 75%, at least 80%, at least 90%, at least 100%, at least 1.5 times, at least 2 times, at least 5 times, at least 10 times, at least 20 times, at least 40 time, at least 60 times, at least 80 times, at least 100 times, or more, compared to the growth rate before the inhibiting step. Non-limiting examples of methods that inhibit algae cell growth may comprise a reduction or a complete depletion of nutrients that are critical for algae growth, or changes in other growth conditions, such as temperature, light, salt concentration, pH, etc. Such nutrients can be water, oxygen, carbon (e.g., $CO_2$), nitrate, phosphate, silicate, vitamins thiamin (B1), cyanocobalamin (B12), biotin, ion, ammonia/ammonium, urea, sodium thiosulphate, etc. Nutrients for algal production are described in Pedersen et al., 1996. In some embodiments, the inhibiting step comprises sudden reduction of carbon source in the growth system. For example, the inhibiting step comprises a shift of $CO_2$ concentration in the growth system from high to low, wherein the shift is sufficient to inhibit algae cell growth/replication partially, or completely. In some embodiments, the $CO_2$ concentration in the system after the shift is about 90%, about 80%, about 70%, about 60%, about 50%, about 40%, about 30%, about 20%, about 10%, about 5%, about 1%, about 0.1%, about 0.01%, about 0.001%, or less of the $CO_2$ concentration before the shift.

The present invention also provides compositions for said methods. In some embodiments, the compositions comprise bicarbonate, and/or at least one agent that can provide bicarbonate when added into the algae growth system. The compositions can in solid form, liquid form, or solid-liquid mixture form.

In some embodiments, the source for bicarbonate in the compositions is a bicarbonate salt. For example, the source is sodium bicarbonate, potassium bicarbonate, ammonium bicarbonate, aminoguanidine bicarbonate, choline bicarbonate, magnesium bicarbonate, or combination thereof. A bicarbonate salt forms when a positively charged ion attaches to the negatively charged oxygen atoms of the ion, forming an ionic compound. Many bicarbonates are soluble in water at standard temperature and pressure, in particular sodium bicarbonate and magnesium bicarbonate. Bicarbonate ion (hydrogen carbonate ion) is an anion with the empirical formula $HCO_3^-$ and a molecular mass of about 61.01 daltons; it consists of one central carbon atom surrounded by three oxygen atoms in a trigonal planar arrangement, with a hydrogen atom attached to one of the oxygens. The bicarbonate ion carries a negative one formal charge and is the conjugate base of carbonic acid, $H_2CO_3$; it is the conjugate acid of $CO_3^{2-}$, the carbonate ion as shown by these equilibrium reactions. One skilled in the art would understand that the following reactions happen in an aquatic solution:

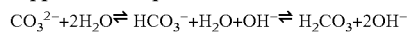

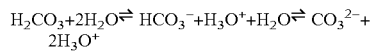

Therefore, in some embodiments of the present invention, a carbonate salt, for example, sodium carbonate, potassium carbonate, ammonium carbonate, aminoguanidine carbonate, choline carbonate, magnesium carbonate, or combination thereof may be used instead of bicarbonate salt in the present invention. The composition provides the algae growth system a concentration of bicarbonate of at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 150 mM, at least 200 mM, at least 250 mM, at least 300 mM or more. The bicarbonate containing and/or bicarbonate-producing composition can be added before, at the time, or after nutrient depletion or growth condition changes that lead to algae growth inhibition. For example, the bicarbonate containing and/or bicarbonate-producing composition is added into the growth system about 1 minute, about 5 minutes, about 10 minutes, about 20 minutes, about half hour, about one hour, about 2 hours, about 3 hours, about 4 hours, about 5 hours, about 6 hours, about 7 hours, about 8 hours, about 8 hours, about 8 hours, about 12 hours, about 24 hours, about 36 hours, about 48 hours, about 60 hours, about 72 hours, about 84 hours, about 96 hours, about 108 hours, about 120 hours, or more before or after nutrient depletion of the growth system or growth condition changes that lead to algae growth inhibition. In some embodiments, to maximize lipid production, it is important that the composition is added into the algae growth system as close to nutrient depletion of the growth system as possible. One skilled in the art would be able to measure, calculate, and/or predict the time point when nutrient depletion happens. For example, the time can be determined by running a control algae growth system without adding the composition.

Besides bicarbonate salts, aerating with a high $CO_2$ concentration and titrating with a base, should change the speciation of $CO_2 \rightarrow HCO_3^-$ in the culture. Thus, $HCO_3^-$ concentration in the culture would be increased and would trigger TAG accumulation. Similarly, a carbonate salt ($CO_3^{2-}$) and an acid could be spiked to form $HCO_3^-$ in the culture (pH would have to be adjusted for bicarbonate formation, for example, adjusted to about pH 8). Therefore, in some embodiments, the step of adding bicarbonate-producing compositions comprises combining $CO_2$ and one or more bases in the growth system, and/or combining one or more carbonate salts ($CO_3^{2-}$) and one or more acids in the growth system. In some embodiments, pH of the growth system is adjusted for the purpose of producing $HCO_3^-$.

The composition further can comprise one or more compounds that can increase the pH of the algae growth system, for example, a base. As used herein, the term "base" refers to an aqueous substance that can accept hydronium ions, or any chemical compound that, when dissolved in water, gives a solution with a hydrogen ion activity lower than that of pure water. Non-limiting examples of bases include, potassium hydroxide (KOH), barium hydroxide ($Ba(OH)_2$), caesium hydroxide (CsOH), sodium hydroxide (NaOH), strontium hydroxide ($Sr(OH)_2$), calcium hydroxide ($Ca(OH)_2$), lithium hydroxide (LiOH), rubidium hydroxide (RbOH), Chloride ion ($Cl^-$), hydrogen sulfate ion ($HSO_4^-$, Nitrate ion ($NO_3^-$), acetate ion ($CH_3COO^-$), hydrogen phosphate ion ($HPO_4^{2-}$), carbonate ion ($CO_3^{2-}$), phosphate ion ($PO_4^{3-}$), and hydroxide ion ($OH^-$). The compounds that can increase the pH of the algae growth system, in some embodiments, increases the pH of the algae growth system to at least 7.5, at least 8.0, at least 8.5, at least 9.0, at least 9.5, at least 10.0, at least 10.5, at least 11.0, or more.

The composition further can comprises one or more pH buffering materials. As used herein, the phrase "pH buffering materials" refers to compositions that when added in a liquid mixture, can maintain the pH of said liquid mixture wherein the pH is kept around about 6.0, about 6.5, about 7.0, about 7.5, about 8.0, about 8.5, about 9.0, about 9.5, about 10.0, about 10.5, about 11.0, about 11.5 or more. Such composition can comprise compounds such as acid, acid salts, basic and basic salts, for example, HCl, $H_2NO_3$, $H_2SO_4$, $NaHCO_3$, NaHS, $NaHSO_4$, $NaH_2PO_4$, $Na_2HPO_4$, $NaHSO_3$, $KHCO_3$, KHS, $KHSO_4$, $KH_2PO_4$, $K_2HPO_4$, $KHSO_3$, NaOH, KOH, $Mg(OH)_2$, $Na_2CO_3$, $K_2CO_3$, $KHCO_3$, $CaCO_3$, $MgCO_3$, $Na_2S$, $K_2S$ et al.

The composition further can comprise an inorganic nitrogen source (e.g., ammonium ($NH_4^+$) containing compounds and nitrate ($NO_3^-$) containing compounds) and/or an organic nitrogen source (e.g., urea, hypoxanthine, guanine, ornithine, glucosamine, and lysine).

The algae in the growth system can be any algae strain. In some embodiments, the algae is an elite algae strain with certain biofuel related industrially important characteristics, such as resistant to stress tolerance, fast replication cycle, higher TAG accumulation ability, etc. In some embodiments, the algae are selected from the group consisting of *Scenedesmus* spp., diatoms (e.g., pennate diatoms), *Botryococcus* spp. (e.g., *B. braunii*), *Chlorella*, *Dunaliella* spp. (e.g., *D. tertiolecta*), *Gracilaria*, *Pleurochrysis* (e.g., *P. carterae*), *Chlorophyta*, and *Sargassum*. In some embodiments, the algae strain is a transgenic algae strain, or a genetically modified algae strain.

The methods of the present invention generally induce the lipid accumulation in algae. In some embodiments, accumulation of at least one type of lipid is induced. For example, triacylglycerol (TAG) accumulation is induced. The methods lead to much higher lipid accumulation in a treated algae growth system compared to a control algae growth system. In some embodiments, the lipid accumulation in the algae growth system is at least 2 times, at least 3 times, at least 4 times, at least 5 times, at least 6 times, at least 7 times, at least 8 times, at least 9 times, at least 10 times, at least 12 times, at least 15 times, at least 20 times, or more of the lipid accumulation in a control algae growth system. As used herein, a control algae growth system is a system under same growth conditions, but without receiving the compositions of the present invention.

Another advantage of the present invention is that it also provides methods of reducing total time required for producing lipid at a predetermined yield from an algae growth system. The methods comprise adding a composition when algae cells in the growth system are in exponential growth stage, but prior to nutrient depletion of the growth system. The composition comprises bicarbonate, and/or one or more compounds that provide bicarbonate after the composition is added into the algae growth system. In some embodiments, the composition further comprises one or more agents that can increase the pH of the algae growth system. In some embodiments, algae cell growth/replication in the growth system is inhibited. In some embodiments, the inhibiting step can happen after the algae in the system enter exponential growth stage, but prior to nutrient depletion of the growth system. In some embodiments, the total time required for producing lipid at a predetermined yield is reduced by at least 10%, at least 20%, at least 30%, at least 40%, at least 50%, at least 60%, at least 70%, at least 80%, at least 90%, at least 100%, or more, compared to the total time required for a control algae growth system.

The present invention also provides methods of increasing lipid accumulation in an algae growth system, comprising growing algae in a medium comprising bicarbonate at the starting point. The inventors discovered that algae growing in a medium comprising bicarbonate at the starting point can accumulate more lipid compared to algae growing in a control system in which little or no bicarbonate is provided at the starting point. A system with little bicarbonate is one having less than 0.0001 mM bicarbonate, or a system having less than 0.001 mM bicarbonate, or a system having less than 0.01 mM bicarbonate. A system having bicarbonate added at the beginning can be a system in which the concentration of bicarbonate in the medium initially is at least 1 mM, at least 5 mM, at least 10 mM, at least 15 mM, at least 20 mM, or more. The algae can be selected from the group consisting of *Scenedesmus* spp., diatoms (e.g., pennate diatoms), *Botryococcus* spp. (e.g., *B. braunii*), *Chlorella*, *Dunaliella* spp. (e.g., *D. tertiolecta*), *Gracilaria*, *Pleurochrysis* (e.g., *P. carterae*), *Chlorophyta*, and *Sargassum*. In some embodiments, the *Scenedesmus* sp. is *Scenedesmus* WC-1 strain, the *Chlorophyta* is *Chlorophyta* sp. EN-2, and the diatom is diatom RGd-1. In some further embodiments, the diatom is diatom Pt-1. The medium can be any medium suitable for algae growth. For example, the medium can be based on ASP II medium. An non-limiting example of ASP II medium is shown in Example 5. One skilled in the art can modify the concentration of each component of the exemplary ASP II medium. In some embodiments, the lipid accumulation in the algae growth system is at least 2 times, at least 3 times, at least 4 times, at least 5 times, at least 6 times, at least 7 times, at least 8 times, at least 9 times, at least 10 times, or more of the lipid accumulation in a control algae growth system.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1

Light and Dark Cycling Affect on pH Induced TAG Accumulation

Inventors' previous studies have detailed how elevated pH can cause TAG accumulation. Furthermore, these studies found that pH and nitrate depletion are independent stress responses and can be utilized either singularly or combined [4, 8]. However, these previous results were collected on cultures growing on a 24 hr light incubation, which naturally inhibits dark cycle respiration while maintaining a continuous photosynthesis rate. FIG. 1 shows growth, pH, and total Nile Red fluorescence for *Scenedesmus* WC-1 grown under ambient air aeration with a 14:10 light-dark cycle using unbuffered Bold's Basal medium. *Scenedesmus* WC-1 was obtained from Yellowstone National Park under Permit No. YELL-2009-SCI-5480. The unbuffered culture maintained exponential growth up to 7 d and exhibited a 0.78 $d^{-1}$ growth rate with a 21 hr doubling time. The culture pH trace shows characteristic increasing pH, for unbuffered medium, during exponential growth up to a maximum of pH 11.3. The total Nile Red fluorescence shows no significant lipid accumulation up to 10 d, after which the fluorescence signal increases to a maximum at 16-18 d. The nitrate became depleted around 9 d and the increase in fluorescence signal after 10 d is attributed to this depletion.

There was an expected pH induced TAG accumulation, when the unbuffered culture pH increased above 10 as previous 24 hr light illumination studies have revealed [4, 8], that is it is evident before nitrate depletion. However, this TAG accumulation was not observed during exponential growth. Insight into the lack of this phenomenon was gained by monitoring pH and Nile Red fluorescence over 24 hours, during late exponential growth prior to nitrate depletion, as shown from day 6 to 7 in FIG. 1. Both fluorescence and pH are at a maximum (1140 arbitrary units and pH 11.0, respectively) right before the light cycle shifts from illuminated to dark, 0 hr, after which the pH and fluorescence decrease until just before the cycle shifts from dark to illuminated (pH 9.4 and 673 units, respectively), at 10 hr. Finally, the light shifts to illuminated leading to an increase back to maximum, pH 11.2 and 1053 units for pH and fluorescence, respectively. The pH decrease during the dark and increase during the light is attributed to CO2 accumulation in the growth medium and photosynthesis, respectively [9]. The Nile Red fluorescence shifts are attributed to dark cycle respiration utilizing TAG for cellular energy and biomass production, along with TAG accumulation during light hours to be used during the dark.

Example 2

Further Investigation of the Light-Dark Cycling Effect on pH-Induced TAG Accumulation in WC-1

Figure 2:
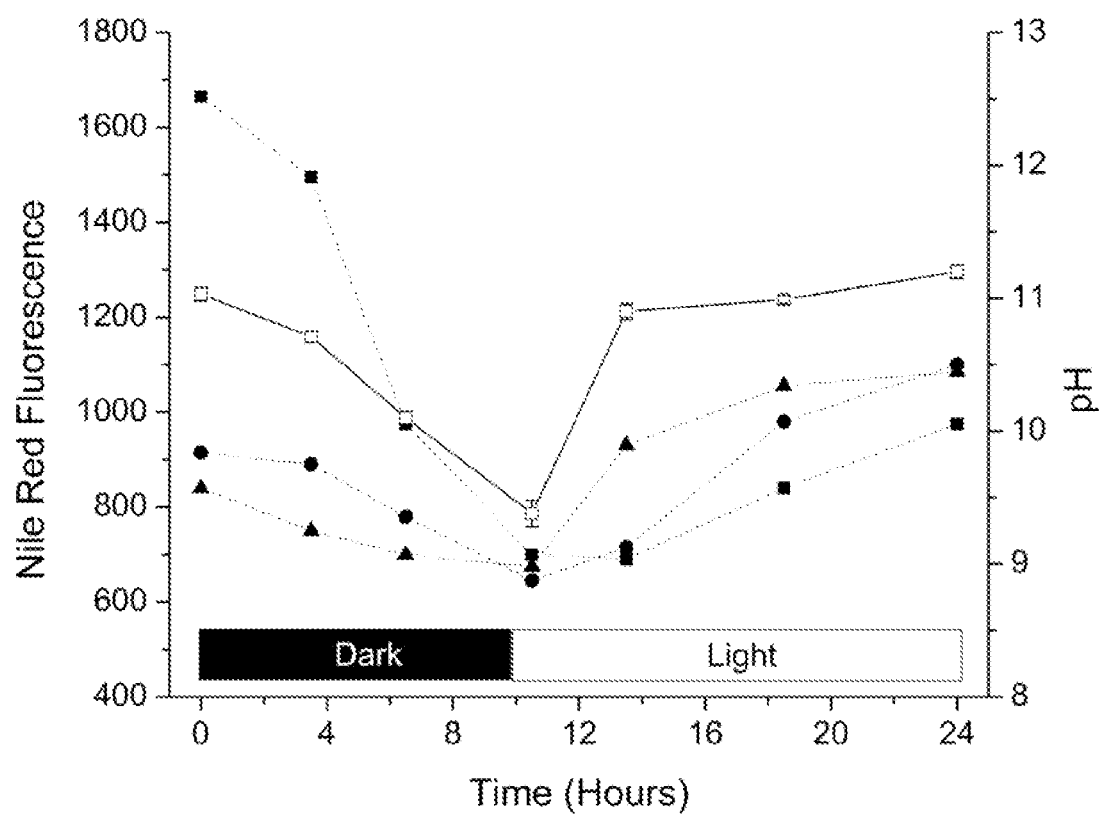
FIG. 2 depicts *Scenedesmus* WC-1 Nile Red fluorescence of three biological replicates (●, ■, and ▲) and average medium pH (□) monitored over 24 hours during late exponential growth (7-8 d) and prior to medium nitrate depletion in unbuffered Bold's basal medium under ambient aeration batch culturing. Bar indicates light and dark times during the 14:10 L:D cycle. n=3

As previous 24 hr light illumination studies have revealed (Gardner et al. 2010; Guckert and Cooksey 1990), there was an expected pH-induced TAG accumulation caused by culture pH increasing above pH 10. However, with 14:10 light cycling this accumulation was not observed during exponential growth, 4-9 d. To understand this lack of TAG accumulation, pH and Nile Red fluorescence were monitored over a 24 hour period during late exponential growth and prior to nitrate depletion. FIG. 2 shows that both Nile Red fluorescence and culture pH are at elevated levels just as the light cycle ends and the dark cycle begins at 0 hr. The pH and fluorescence decreased until the cycle was shifted from dark to light 10 hr later. The illumination caused an increase in both pH and Nile Red fluorescence. The pH decrease during the dark and increase in the light can be attributed to carbonic acid accumulation and photosynthesis, respectively (Shiraiwa et al. 1993). The decrease in Nile Red fluorescence correlates to dark cycle respiration utilizing TAG for cellular energy. TAG synthesis was observed during light hours. This trend of cellular TAG accumulation and utilization has previously been observed in *Chlorella* CHLOR-1, and our results corroborate the hypothesis that TAG accumulates during light exposure followed by utilization in the dark (Thomas 1990).

FIG. 2 shows the medium pH decreased to 9.4 during the dark hours. Previous studies of WC-1 have shown that CHES buffered cultures (pKa 9.3) did not accumulate TAG under this condition (Gardner et al. 2010). Therefore, this lower pH during the dark hours is likely why WC-1 does not accumulate TAG during the late exponential growth, even though pH reached 11.3 in the light cycle. It is important to state that Nile Red fluorescence depends on the TAG content of the cells and not on the pH of the medium. It has been observed that, cell viability is preserved using the Nile Red staining method (Cooksey et al. 1987), and it is expected that these intact cells maintain a constant internal pH independent of the medium pH. Further, Nile Red fluorescence is correlated directly with GC analysis of the extracted lipid and is independent of medium pH, $R^2=0.95$ for WC-1 (Gardner et al. 2010). Taken together, these studies indicate Nile Red fluorescence is not correlated directly with pH during TAG analysis, but is correlated to cellular TAG content which in turn is caused by metabolic shifts induced from pH changes.

Example 3

Growth Kinetics During Increased Aeration $CO_2$ Concentration

Figure 3:
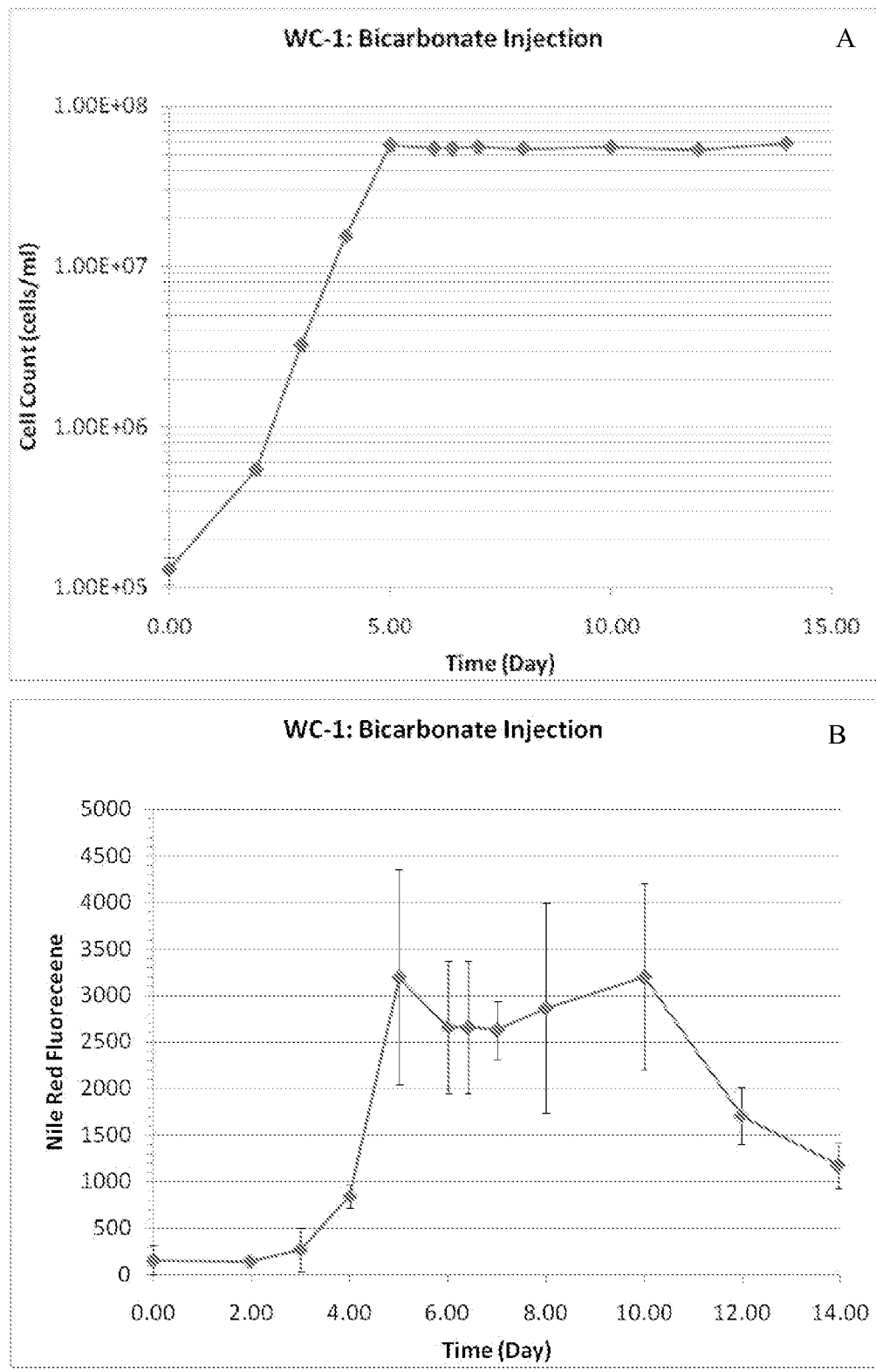
FIG. 3 depicts average cell density and Nile Red Fluorescence of *Scenedesmus* WC-1 grown on 14:10 L:D cycle in unbuffered Bold's Basal Medium, 5% CO2 aeration. Error is standard deviation. n=3

The inventors sought to improve the growth kinetics of WC-1 by increasing the $CO_2$ concentration from ambient air (0.04%) to 5%. FIG. 3 shows the growth and total Nile Red fluorescence during high $CO_2$ aeration. The culture grew exponentially to 5 d with a growth rate of 1.53 $d^{-1}$ and a 10.9 hr doubling time. The medium pH maintained a near constant value of 6.9±0.15 throughout the experiment and the nitrate became depleted at 4 d. After 4 d the Nile Red fluorescence shifted to an elevated value. The total fluorescence signal was much smaller compared to low $CO_2$ (ambient air) growth, FIG. 1. After 10 d the fluorescence signal began to decrease, indicating the cellular TAG was being utilized or degraded.

It is apparent that high $CO_2$ concentrations dramatically increase WC-1's growth rate, however this causes the culture pH to remain low and low pH at the time of nitrate depletion has been shown to correlate with low TAG accumulation in WC-1 [4]. This indicates a growth scenario where high $CO_2$ aeration is utilized during exponential growth, and just prior to nitrate depletion the culture is shifted to air only aeration which was shown to increase culture pH. Furthermore, the culture TAG accumulation can be increased if higher pH is maintained during the dark hours in the light:dark cycle.

Example 4

Figure 4:
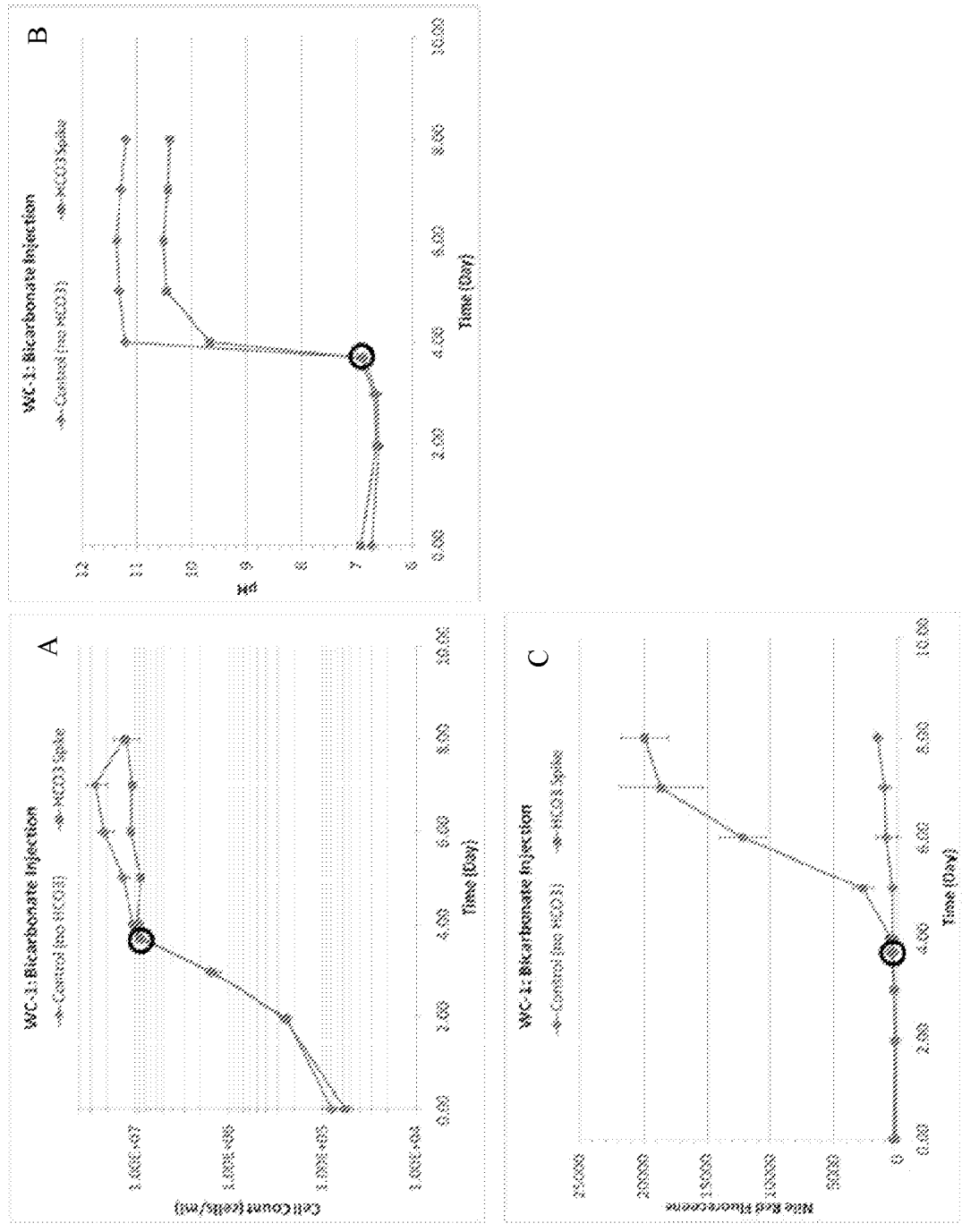
FIG. 4 depicts average cell density (A), medium pH (B), and Nile Red Fluorescence (C) of *Scenedesmus* WC-1 grown on 14:10 L:D cycle in unbuffered Bold's Basal Medium, 5% CO2 aeration switched to ambient air aeration, with and without 50 mM $HCO_3$ spike. Black circles indicate time of bicarbonate spike and error is standard deviation. n=3

Growth and TAG Accumulation in High $CO_2$ Shifted to Ambient Air, with and without Bicarbonate Injection Cellular TAG accumulation, after shifting from high (5% $CO_2$) to low (ambient air) $CO_2$ aeration, was investigated with and without added bicarbonate. FIG. 4 shows growth, pH, and total Nile Red fluorescence of WC-1, with and without a bicarbonate spike to final concentration of 50 mM. Before nitrate depletions both cultures grew exponentially with a 2.05 $d^{-1}$ growth rate and a doubling time of 8.1 hr. Nitrate became depleted just after 4 d for both cultures. One culture was designated for bicarbonate spike while the other acted as control, both cultures had the high-to-low $CO_2$ aeration shift at the time of bicarbonate spike (just prior to nitrate depletion). The spike occurred at 3.7 d with 67.1 mg $L^{-1}$ nitrate remaining (221.5 mg $L^{-1}$ nitrate initially), and immediately stopped cell doubling. The "no spike" control shifted to slower growth rate and continued to grow (1.6 doublings), until there was surfactant formation (foaming) and the culture had to be collected.

Both cultures maintained a pH of 6.75±0.14 until time of bicarbonate spike, after which the bicarbonate spike culture and the no spike control shifted to a maximum pH of 10.5 and 11.4, respectively. Furthermore, both cultures became nitrate depleted shortly after 4 d. The total Nile Red fluorescence, for the bicarbonate spike culture, began to increase at 5 d and reached 20,000 units 4 days later. In contrast, the fluorescence for the no spike control only increased to 1500 units.

Figure 5:
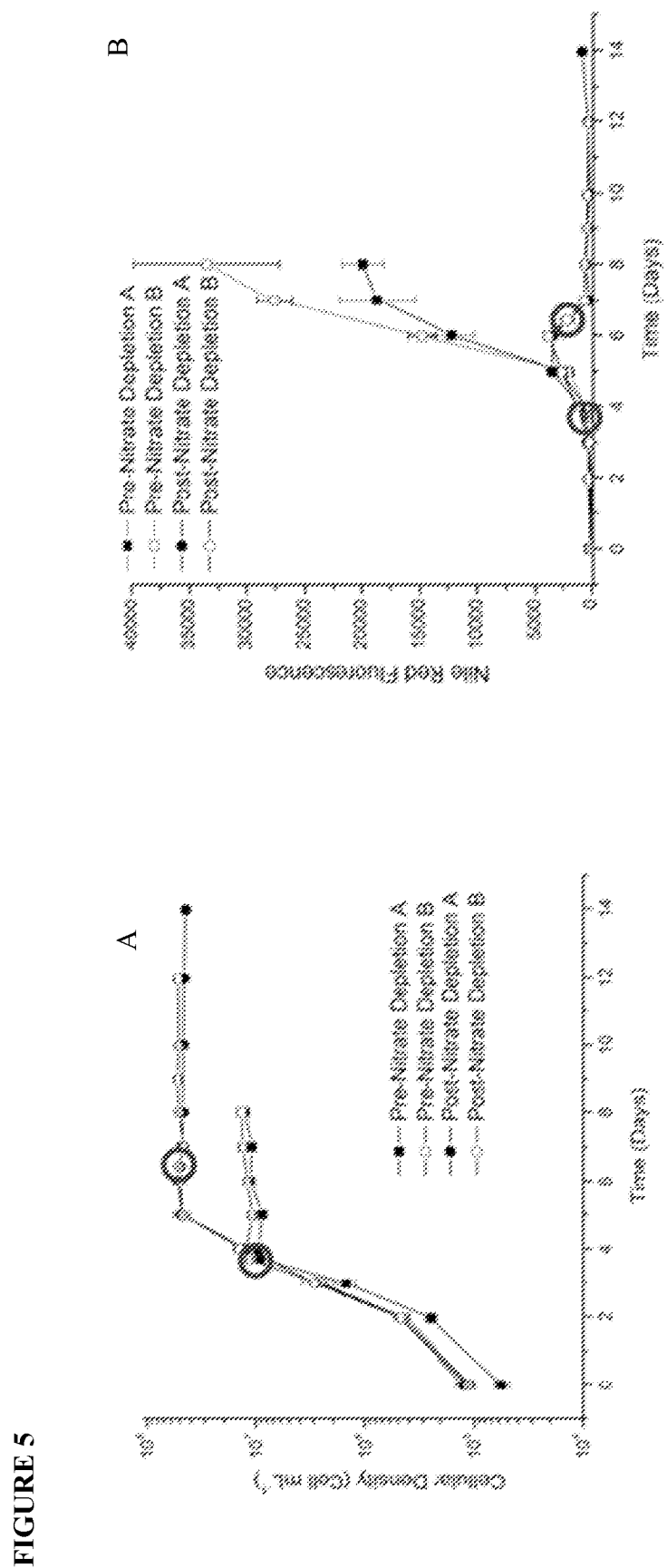
FIG. 5 depicts results of bicarbonate spike treatments. Average cell density (A) and Nile Red Fluorescence (B) of *Scenedesmus* WC-1 grown in 14:10 L:D cycle and unbuffered Bold's Basal Medium, 5% CO2 aeration until bicarbonate was added (circles), then aeration was changed to ambient air aeration. Error is standard deviation. n=3

Bicarbonate spike effects were further investigated, and verified by experimental replication, by adding bicarbonate after medium nitrate depletion, when the cells are in a stationary growth phase. FIG. 5 shows cellular growth and total Nile Red fluorescence of WC-1 (bicarbonate added before nitrate depletion and at 6 d, post medium nitrate depletion). The culture grew exponentially under 5% $CO_2$ aeration with a 1.53 $d^{-1}$ growth rate and a doubling time of 10.9 hr. Furthermore the cultures became nitrate depleted at 4 d causing a Nile Red fluorescence increase to 3500 units at 5 d. At 6 d the culture was spiked with bicarbonate to a final concentration of 50 mM and the aeration was adjusted to normal ambient air (low $CO_2$). The aeration flow rates were the same.

The added bicarbonate immediately shifted the pH to 9.1 and the culture reached a maximum pH of 10.0 in one day. The culture Nile Red fluorescence signal decreased to baseline indicating that when spiked with bicarbonate 2 days after nitrate depletion, lipids that had accumulated were metabolized.

Cellular metabolic response, with respect to bicarbonate transportation and growth, has previously been studied in green algae [10-13]. Furthermore, *Scenedesmus obliquus* has been shown to have two carbon concentrating mechanisms in addition to passive $CO_2$ diffusion [13]. However, to our knowledge, no one has investigated the effects bicarbonate has on TAG accumulation. Clearly these results point to a trigger that is capable of stopping cell growth/replication and induce TAG accumulation. Of particular interest is the ability to reach a maximum Nile Red fluorescence signal after 3-4 d, compared with 8-10 d under ambient air aeration with no bicarbonate spike. This reduced the total time required for TAG accumulation significantly.

Example 5

Additional Experiments with WC-1 Growth and TAG Accumulation with 5% $CO_2$ Shifted to Ambient Air, with and without Bicarbonate Addition Cultures were grown with 5% $CO_2$ until nitrate depletion was imminent. After shifting from 5% $CO_2$ to ambient air for aeration, cellular TAG accumulation, with and without addition of bicarbonate (50 mM), was investigated. FIG. 6 shows the growth (a), total Nile Red fluorescence (b), and medium pH (c) of WC-1, with and without a 50 mM bicarbonate addition when aeration is shifted from 5% $CO_2$ to ambient aeration at the time of nitrate depletion. Before nitrate depletion, both cultures grew exponentially with a specific growth rate of 2.1 $d^{-1}$ and a doubling time of 8.1 hr. Nitrate was depleted at 4 d for both cultures. The bicarbonate was added at 3.7 d when there was 3.4 mg $L^{-1}$ nitrate remaining (200 mg $L^{-1}$ nitrate initially), and it stopped cellular replication immediately. With nitrate depletion, the bicarbonate-free control shifted into slower growth rate and continued to double 1.6 times.

Both cultures maintained a pH of 6.75±0.14 until the bicarbonate addition, after which the bicarbonate addition culture and the bicarbonate-free control shifted to a maximum pH of 10.4 and 11.4, respectively. For the bicarbonate addition culture, the total Nile Red fluorescence began to increase at 5 d and reached 33,500 units 3 days later. In contrast, the fluorescence for the control culture, unsupplemented with bicarbonate, increased to only 1500 units. Comparison of the bicarbonate supplemented culture with the ambient aerated culture shows maximum total Nile Red fluorescence was reached in only 8 d instead of 16-18d. Using high $CO_2$ during the initial exponential growth contributed to the decreased culturing time needed to reach nitrate depletion. However, when bicarbonate was added, the rate of TAG accumulation was twice as fast which contributed to the decreased culturing time for maximum TAG accumulation. Table 1 compares biomass and TAG yields for WC-1 under the different culture conditions. Of particular note, WC-1 reached similar total Nile Red fluorescence when grown on air only compared to cultures with bicarbonate added at nitrate depletion. However in the air only culture, there are almost twice as many cells and it took 10 days longer to accumulate maximum TAG. Thus, there is more TAG per cell in the bicarbonate added culture and the specific Nile Red fluorescence indicates this difference.

Figure 7:
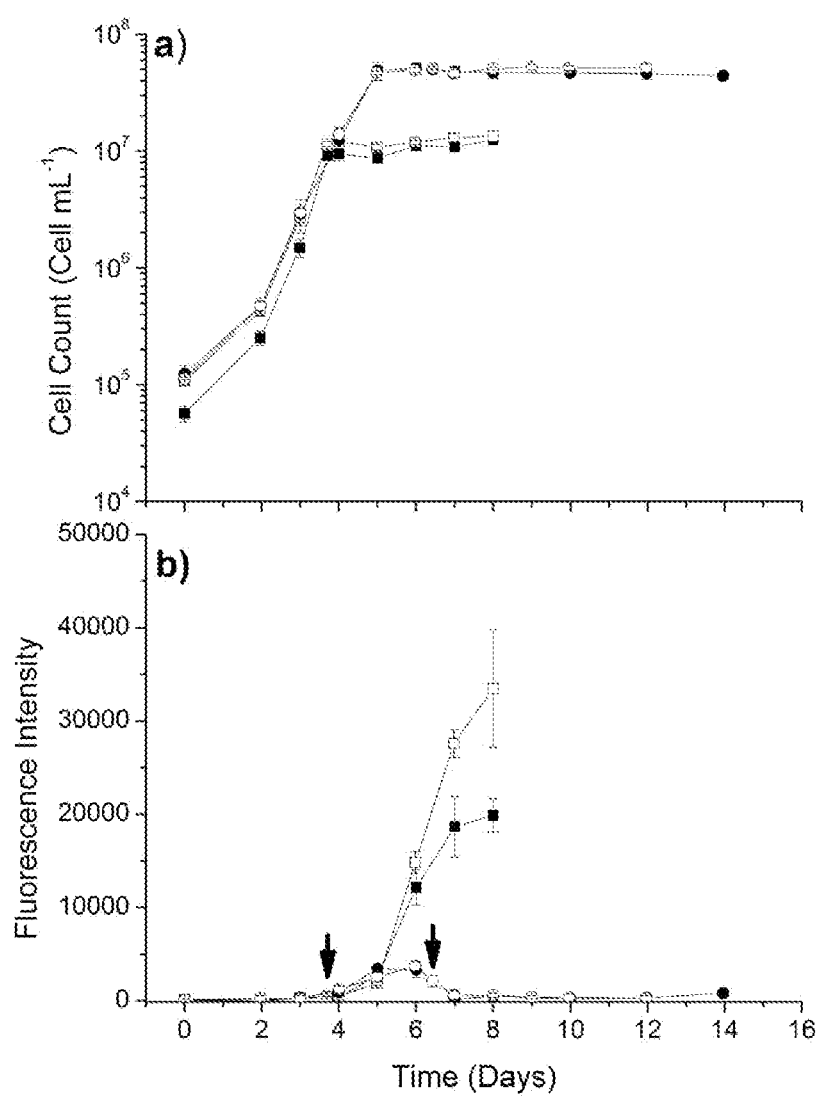
FIG. 7 depicts average and standard deviation of cellular growth (a) and total Nile Red fluorescence intensity (b) of *Scenedesmus* WC-1 aerated with 5% $CO_2$ in air that is switched to ambient air and 50 mM bicarbonate addition pre-nitrate depletion (■ and □) or post-nitrate depletion (● and ○). Arrows indicate time of bicarbonate addition. Growth was maintained in unbuffered Bold's basal medium illuminated with a 14:10 L:D cycle. n=3

The addition of bicarbonate to the culture at the time of nitrate depletion clearly changed the metabolic activity of the culture. Immediately after bicarbonate addition WC-1 stopped cellular replication and began to accumulate TAG. The timing of this effect was further investigated by comparing effects of bicarbonate addition before nitrate depletion and bicarbonate addition after the medium was nitrate depleted, where cultures were in the stationary phase. FIG. 7 shows the cellular growth and total Nile Red fluorescence of unbuffered WC-1 when bicarbonate is added before nitrate depletion and at 6.4 d when the nitrate has been depleted. Cultures grew exponentially under 5% $CO_2$ aeration with a 1.9 $d^{-1}$ specific growth rate and a doubling time of 8.7 hr. Cultures became nitrate depleted at 4 d. The cultures to which bicarbonate was added at 3.7 d (pre-nitrate depletion) showed an immediate stop in cellular replication. Furthermore, these cultures accumulated TAG from 5-8 d. There was a difference in nitrate concentration at the time of bicarbonate addition, due to differences in inoculum concentration, which may have affected the final TAG concentration at 8 d. These results suggest an optimal time of nitrate concentration, at which the bicarbonate should be added.

When the cultures were maintained on 5% $CO_2$ until after nitrate depletion at 4 d, the Nile Red fluorescence increased to 3500 units at 5 d presumably due to nitrate depletion. This initial increase is comparable to the fluorescence increase observed in the 5% $CO_2$ control of FIG. 6. At 6.4 d bicarbonate aeration was adjusted to ambient air (low $CO_2$) and bicarbonate was added (50 mM final concentration). The cultures to which bicarbonate was added immediately shifted the pH to 9.1 and the culture reached a maximum pH of 10.0 over the remainder of the experiment. Nile Red fluorescence of these cultures decreased to baseline (450 units) indicating that accumulated lipids were consumed and no significant TAG accumulation was observed throughout the remainder of the experiment.

Table 1 summarizes final culture characteristics for the experiments performed on *Scenedesmus* WC-1. It can be seen that when the final Nile Red fluorescence is divided by the population density, the pre-nitrate depletion bicarbonate triggered cultures have the highest TAG per cell (specific Nile Red fluorescence).

TABLE 1

Comparison of average and standard deviation in culture growth and lipid production properties of WC-1 and Pt-1 cultured in unbuffered Bold's basal and ASP II media, respectively, during 14:10 light-dark cycling. n = 3

| Organism | Aeration | Time of $HCO_3$ Addition (d) | Time of Harvest (d) | Final Cell Density (×10$^7$ cells mL$^{-1}$) | Dry Weight (g/L) (DCW)a | Final Total Nile Red Fluorescence (×10$^3$ units) | Final Specific Nile Red Intensity Cell$^{-1}$b |
|---|---|---|---|---|---|---|---|
| *Scenedesmus* WC-1 | Air | N/A | 18.0 | 2.46 ± 0.06 | 1.1 ± 0.1 | 36.8 ± 5.2 | 15.0 ± 2.3 |
|  | 5% $CO_2$ | N/A | 14.0 | 5.87 ± 0.15 | 2.7 ± 0.1 | 1.2 ± 0.2 | 0.2 ± 0.1 |
|  | 5% $CO_2$ | N/A | 8.0 | 2.69 ± 0.69$^e$ | 0.8 ± 0.1 | 1.0 ± 0.4$^e$ | 0.4 ± 0.1$^e$ |
|  | 5% $CO_2$ → Air | 3.7$^c$ | 8.0 | 1.34 ± 0.15 | 1.1 ± 0.1 | 33.5 ± 6.3 | 24.8 ± 2.2 |
|  | 5% $CO_2$ → Air | 6.4$^d$ | 12.0 | 5.18 ± 0.41 | 2.1 ± 0.0 | 0.3 ± 0.3 | 0.1 ± 0.1 |

TABLE 1-continued

Comparison of average and standard deviation in culture growth and lipid production properties of WC-1 and Pt-1 cultured in unbuffered Bold's basal and ASP II media, respectively, during 14:10 light-dark cycling. n = 3

| Organism | Aeration | Time of HCO$_3$ Addition (d) | Time of Harvest (d) | Final Cell Density (×10$^7$ cells mL$^{-1}$) | Dry Weight (g/L) (DCW)a | Final Total Nile Red Fluorescence (×10$^3$ units) | Final Specific Nile Red Intensity Cell$^{-1}$b |
|---|---|---|---|---|---|---|---|
| Phaeodactyhan | Air | N/A | 9.0 | 1.17 ± 0.04 | 0.2 ± 0.0 | 0.6 ± 0.4 | 0.3 ± 0.2 |
| Pt-1 | Air | 3.0c | 9.0 | 0.65 ± 0.01 | 0.1 ± 0.0 | 6.5 ± 0.9 | 9.9 ± 0.8 |
|  | Air | 7.0d | 9.0 | 1.02 ± 0.05 | 0.1 ± 0.0 | 0.1 ± 0.1 | 0.1 ± 0.1 | aDry cell weight (DCW) determined gravimetrically with filtered samples dried at 60° C.
bCalculated by fluorescence signal/cell density × 10,000 (scaling factor)
cPre-nitrate depletion
dPost-nitrate depletion
e7 d reported due foaming at 8 d (time of harvest)

Example 6

Preliminary Assessment of Bicarbonate Spike Effect on TAG Accumulation in a Pennate Diatom RGd-1

Figure 8:
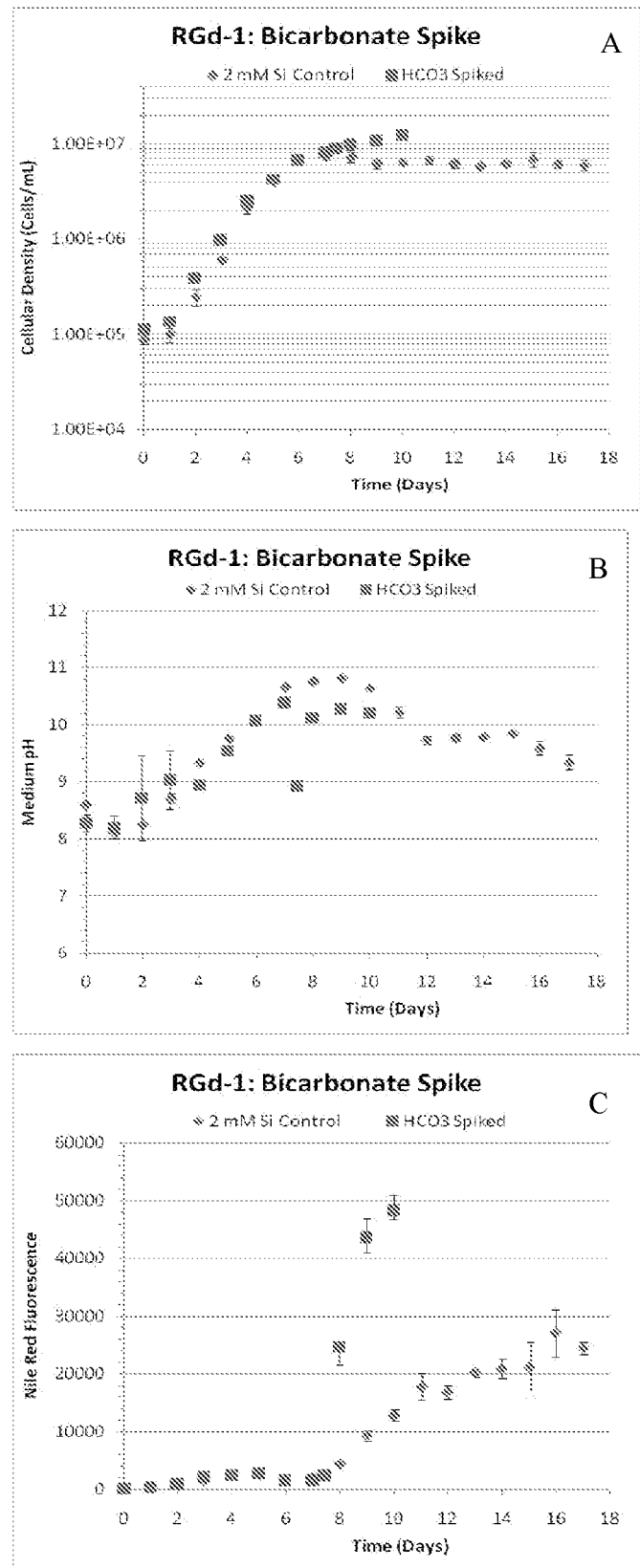
FIG. 8 depicts average cell density (A), medium pH (B), and Nile Red Fluorescence (C) of diatom RGd-1 grown on 14:10 L:D cycle in unbuffered Bold's Basal Medium with 2 mM $Na_2SiO_3.9H_2O$, 1.5 nM cyanocobalamin (B12), and S3 vitamins from ASP II medium recipe, ambient air aeration, with and without 25 mM $HCO_3$ spike. Culture was spiked at 7.4 d, near Si depletion, and error is standard deviation. n=3 for no spike control and n=2 for bicarbonate spiked culture.
Figure 9:
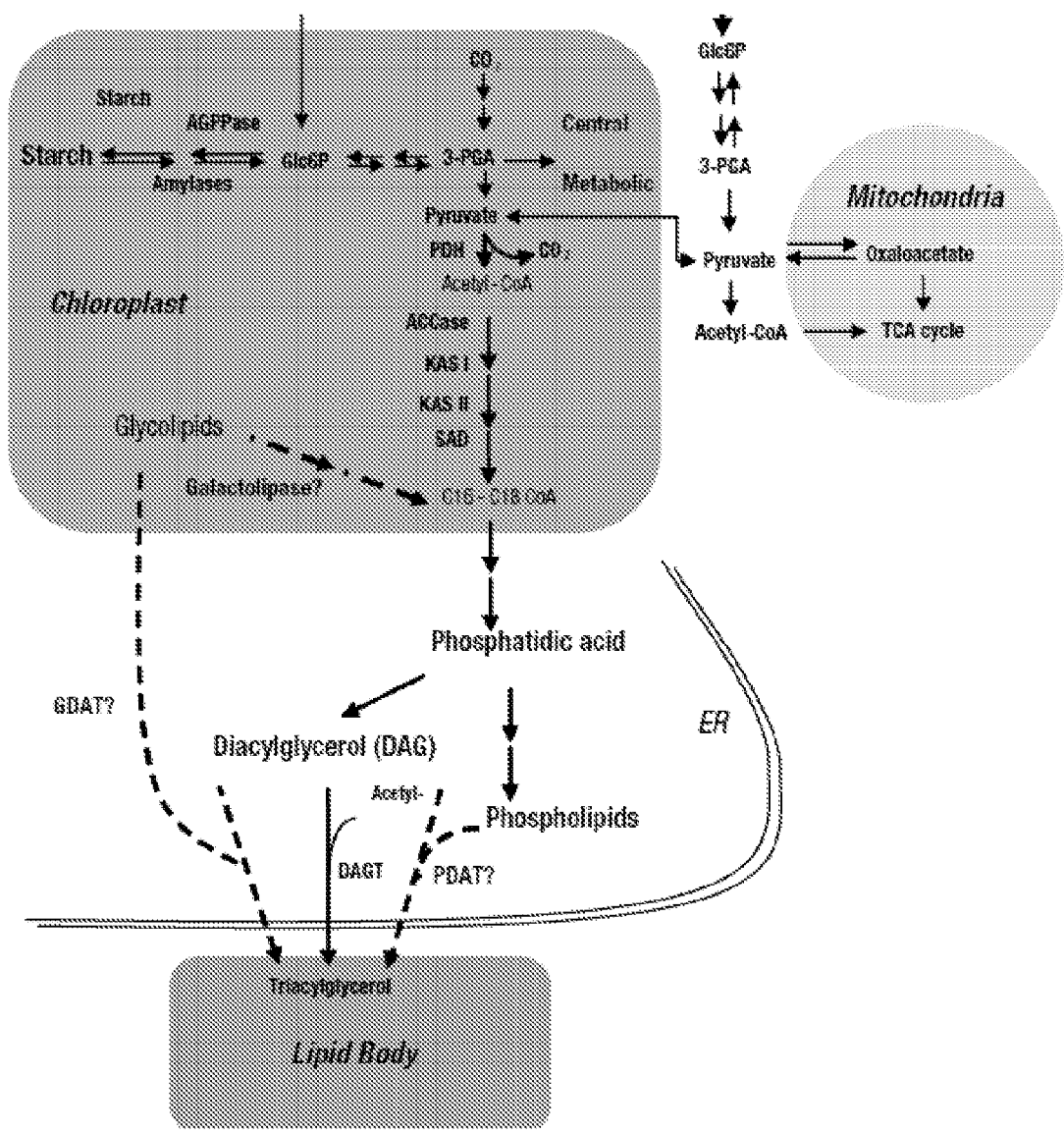
FIG. 9 depicts major pathways for fatty acid synthesis in plants and algae. 3-PGA: 3-phosphoglycerate; Accase: acetyl CoA carboxylase; ACP: acyl carrier protein; AGPPase: ADP glucose pyrophosphorylase; ER: Endoplasmic reticulum; GDAT: putative glycolipids: DAG acyltransferase; Glc6P: glucose-6-phosphate; KAS: 3-ketoacyl-ACP; PDAT: Phospholipids: DAG acyltransferase; PDH: pyruvate dehydrogenase (putative pathways were proposed in dashed lines).

The generality of bicarbonate spike effect was tested by analyzing the TAG accumulation response of a diatom RGd-1. FIG. 8 shows growth, pH, and total Nile Red fluorescence, of diatom RGd-1, with and without a bicarbonate spike to final concentration of 50 mM, grown in Bold's Basal medium with an enhanced silicate concentration. RGd-1 was obtained from Yellowstone National Park under Permit No. YELL-2009-SCI-5480. These cultures were illuminated with 14:10 light-dark cycling with ambient air aeration. The two cultures grew with similar growth rates until 7.4 d when the bicarbonate spike was introduced. Within 2-3 d of the bicarbonate spike the total Nile Red fluorescence increased 10-fold over the no spike control. There was a significant fluorescence increase in the control culture that is attributed to silicon limitation. However, the important features of using the bicarbonate trigger are the higher degree and lower culture time required to accumulate the TAG.

Example 7

Preliminary Assessment of Bicarbonate Effect on TAG Accumulation in a Diatom *Phaeodactylum Tricornutum* Pt-1

The effects of adding bicarbonate at the starting point of algae growth were tested by analyzing the TAG accumulation response of a diatom (*Phaeodactylum tricornutum*, strain Pt-1 [35-36], the Provasoli-Guillard National Center for Culture of marine Phytoplankton culture collection CCMP 2561). This strain was harvested off Blackpool, UK, ca. 1956 and identified by S. Coughlan.

The diatom was cultured in ASP II medium, with or without adding NaHCO$_3$ under 14:10 L:D cycle at 22° C. A non-limiting example of ASP II medium is shown below:

ASP II Medium:

ASP-II Media Composition

| Component | MW | Stock Solution (g/L) | Quantity Used (g or mL) | Concentration in Final Medium (M) |
|---|---|---|---|---|
| NaCl | 58.45 | — | 18.00 g | 3.08E−01 |
| MgSO$_4$*7H$_2$O | 246.48 | — | 5.00 g | 2.03E−02 |
| KCl | 74.55 | — | 0.60 g | 8.05E−03 |
| CaCL$_2$*2H$_2$O | 147.01 | — | 0.735 g | 5.00E−03 |
| Tris | 145.80 | — | 1.17 g | 8.00E−03 |
| Na$_2$EDTA | 372.24 | — | 0.03 g | 8.06E−05 |
| NaNO$_3$ | 84.99 | — | 0.05 g | 5.90E−04 |
| H$_3$BO$_3$ | 61.83 | 34 | 1 mL | 5.50E−04 |
| Na$_2$SiO$_3$*9H$_2$O | 284.19 | 150 | 1 mL | 5.28E−04 |
| K$_2$HPO$_4$ | 174.18 | 5 | 1 mL | 2.87E−05 |
| FeCl$_3$*6H$_2$O | 270.20 | 3.840 | 1 mL | 1.42E−05 |
| ZnCl$_2$ | 136.30 | 0.313 | 1 mL | 2.30E−06 |
| MnCl$_2$*4H$_2$O | 197.90 | 4.320 | 1 mL | 2.18E−05 |
| CoCl$_2$*6H$_2$O | 237.93 | 0.012 | 1 mL | 5.09E−08 |
| CuCl$_2$*2H$_2$O | 170.48 | 0.003 | 1 mL | 1.89E−08 |
| Cyanocobalamin (B12) | 1355.36 | 0.002 | 1 mL | 1.4800E−09 |
| S3 Vitamin Solution |  | see below | 1 mL | — |

| S3 Vitamin Solution | |
|---|---|
| Component | Quantity Used (g/L) |
| Inositol | 5 g |
| Thymine | 3 g |
| Thiamine*HCl (B1) | 0.5 g |
| Nicotinic acid (niacin) | 0.1 g |
| Ca pantothenate | 0.1 g |
| p-Aminobenzoic acid | 0.01 g |
| Biotin (vitamin H) | 0.001 g |
| Folic Acid | 0.002 g |

Figure 10:
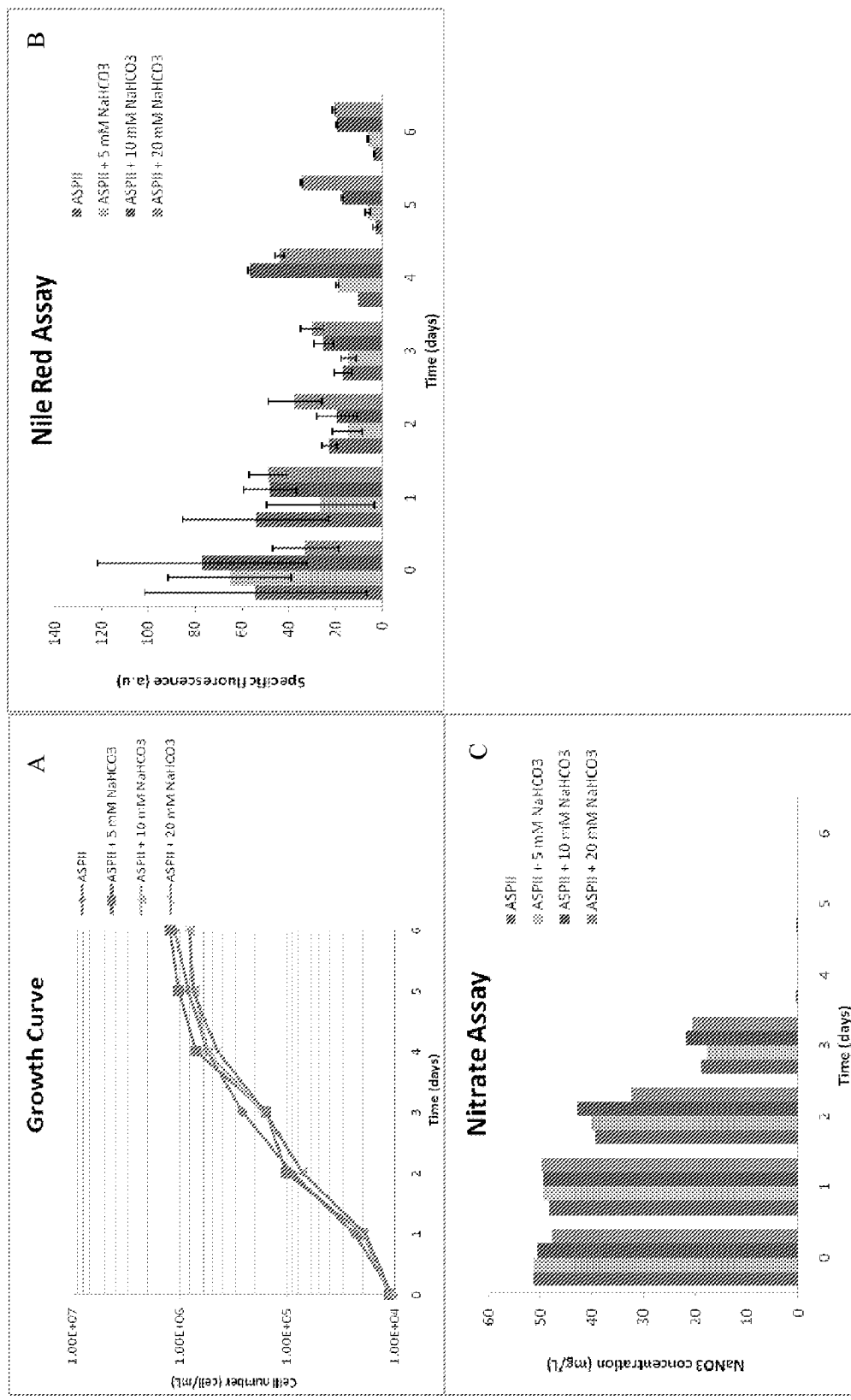
FIG. 10 depicts cell growth (A), Nile Red Fluorescence (B), and nitrate assay (C) of *Phaeodactylum tricornutum* Pt-1 (Pt-1) grown on 14:10 L:D cycle in ASP II medium. 5 mM, 10 mM, or 20 mM bicarbonate were provided at the starting point of algae growth.

FIG. 10 shows cell growth, total Nile Red fluorescence, and nitrate depletion as measured with a nitrate assay for diatom Pt-1, with and without 5 mM, 10 mM, or 20 mM NaHCO$_3$ added in the culture media from the starting point. As the results indicate, in all cases, addition of bicarbonate from the beginning of the experiment stimulated more lipid production compared to cultures that did not have bicarbonate in them.

Example 8

Preliminary Assessment of Bicarbonate Spike Effect on TAG Accumulation in a Diatom *Phaeodactylum Tricornutum* Pt-1

Figure 11:
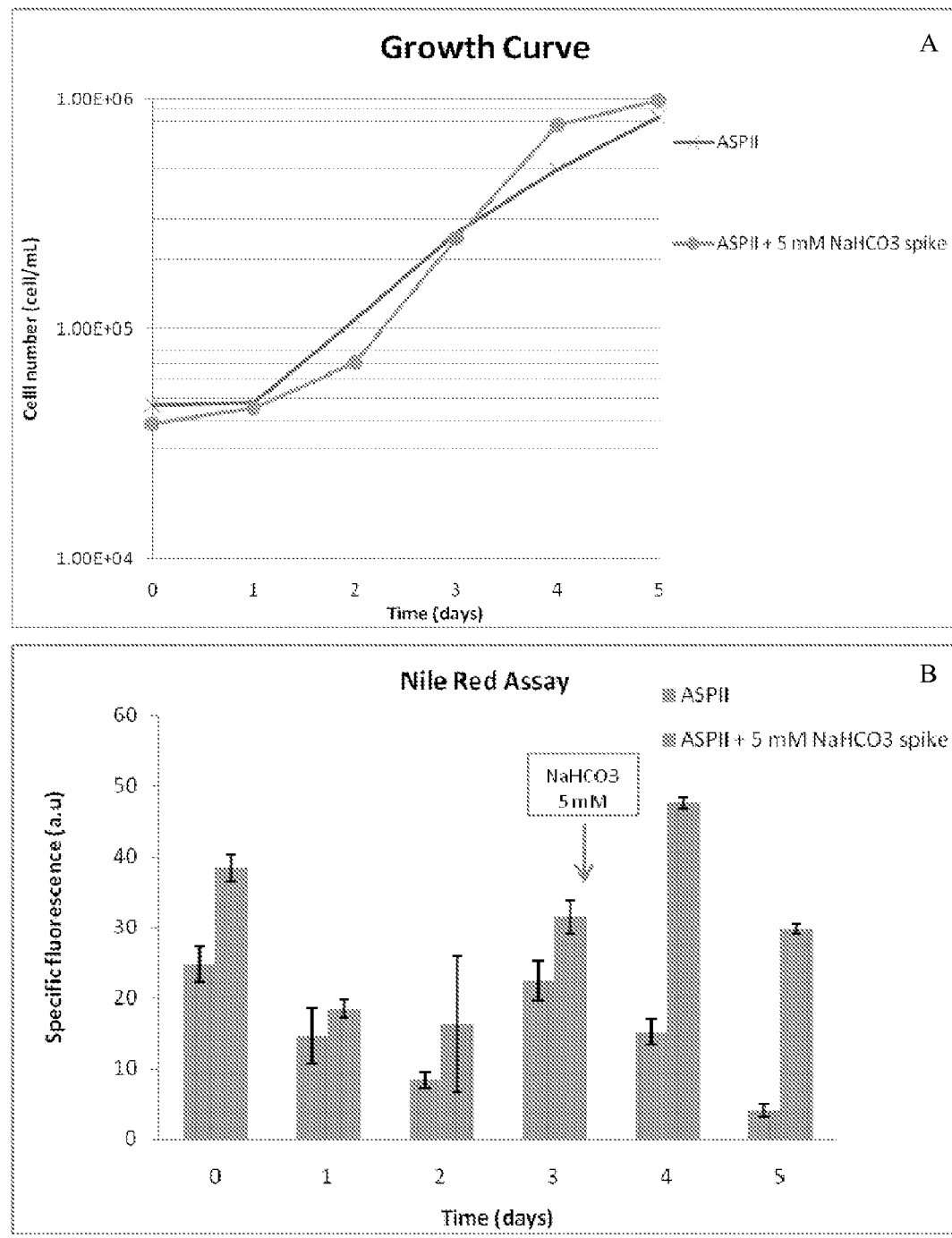
FIG. 11 depicts average cell density (A) and Nile Red Fluorescence (B) of diatom *Phaeodactylum tricornutum* Pt-1 grown on 14:10 L:D cycle in ASP II Medium, with and without 5 mM $HCO_3$ spike on day 3.

The generality of bicarbonate spike effect was tested by analyzing the TAG accumulation response of diatom Pt-1. FIG. 11 shows cell growth and total Nile Red Fluorescence of diatom Pt-1, with and without a bicarbonate spike of concentration of 5 mM, grown in ASP II medium. These cultures were illuminated with 14:10 light-dark cycling. NaHCO$_3$ was added in the third day before nitrate depletion. There was a significant fluorescence increase in the culture treated with bicarbonate spike.

Figure 12:
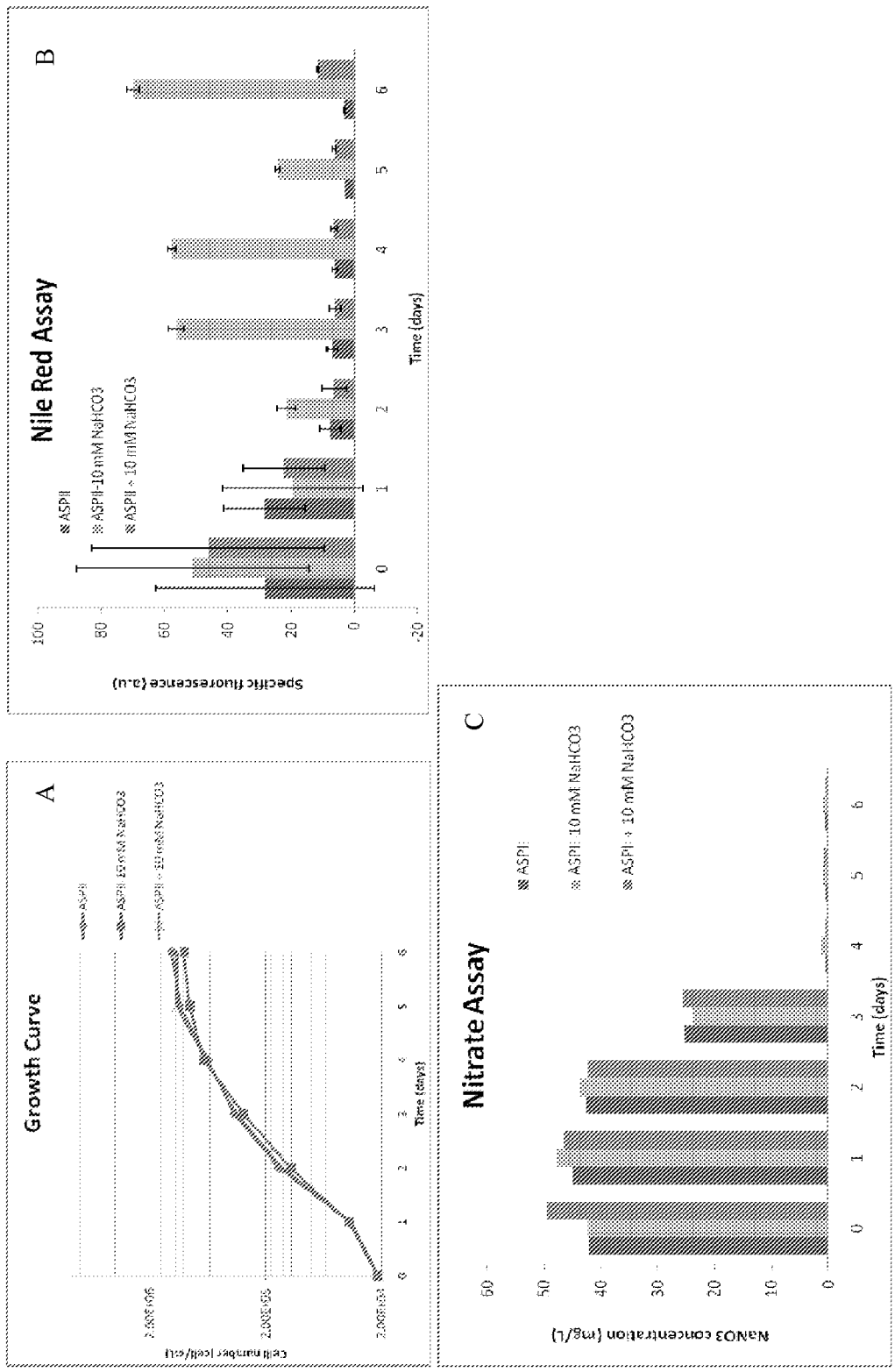
FIG. 12 depicts average cell density (A), Nile Red Fluorescence (B), and nitrate assay (C) of diatom *Phaeodactylum tricornutum* Pt-1 grown on 14:10 L:D cycle in ASP II Medium, with and without 10 mM $HCO_3$ spike either before (ASP II—10 mM $NaHCO_3$, spike at day 3) or after (ASP II+10 mM $NaHCO_3$, spike at day 5) nitrate depletion.

In another experiment, bicarbonate spike was induced by adding 10 mM NaHCO$_3$ either before or after nitrate depletion. FIG. 12 shows cell growth, Nile Red Fluorescence, and nitrate assay of diatom Pt-1, with a bicarbonate spike before (ASP II—10 mM NaHCO$_3$, spike at day 3) or after (ASP II+10 mM NaHCO$_3$, spike at day 5) nitrate depletion. The results indicate that a spike before nitrate depletion increases lipid accumulation in diatom Pt-1, while a spike after nitrate depletion does not.

Example 9

Figure 13:
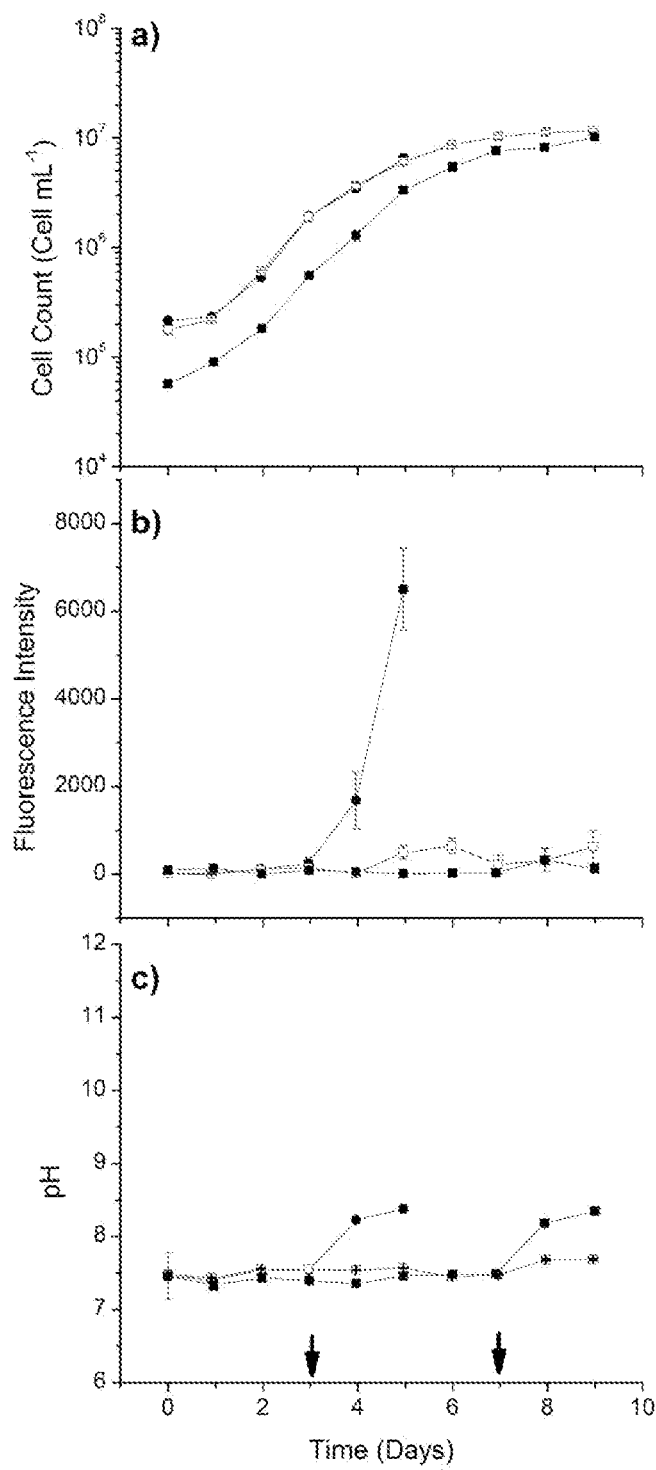
FIG. 13 depicts average and standard deviation of cellular growth (a), total Nile Red fluorescence intensity (b), and culture pH (c) of *Phaeodactylum tricornutum* Pt-1 aerated with ambient air and 25 mM bicarbonate addition pre-nitrate depletion (●), added post-nitrate depletion (■), and no addition (□). Arrow indicates time of bicarbonate addition. Growth was maintained in 50 mM Tris (pKa 7.8) buffered ASP II medium illuminated with a 14:10 L:D cycle. n=3

Further Assessment of Growth and TAG Accumulation in *Phaeodactylum Tricornutum* Pt-1 with and without Bicarbonate Addition To ascertain whether bicarbonate addition would give similar results in other algae, the marine diatom *P. tricornutum* Pt-1 was studied in a similar manner to WC-1. However, the final concentration of bicarbonate addition was decreased from 50 mM to 25 mM, and 50 mM Tris buffer (pKa 7.8) was incorporated to minimize pH shifts because as the pH approaches pH 9.0, the constituents of the ASP II medium precipitate which could potentially confound results. Furthermore, ambient aeration was maintained throughout incubation because 5% CO$_2$ causes a decrease in culture pH which significantly inhibited cellular growth (data not shown). FIG. 13 shows cellular growth (a), total Nile Red fluorescence (b), and medium pH (c), of Pt-1, with and without 25 mM bicarbonate addition, both pre- and post-nitrate depletion. All cultures grew exponentially with a 0.9 d$^{-1}$ specific growth rate and a doubling time of 18.4 hr. Nitrate became depleted at 4 d for the control and pre-nitrate bicarbonate triggered cultures, while the post-nitrate depletion triggered cultures became nitrate depleted at 6 d (due to the lower inoculum concentration). Bicarbonate was added at 3 d and 7 d for the pre- and post-nitrate depleted cultures, respectively. Similar to WC-1, Nile Red fluorescence increased significantly when bicarbonate was added while the medium still had nitrate, but did not increase when no nitrate was available. However, unlike WC-1, cell replication was not inhibited by the addition of bicarbonate. Previous experimentation with Pt-1 indicated that Nile Red fluorescence decreased after two days of TAG accumulation, therefore the culture was harvested on the second day after bicarbonate addition, i.e. 5 d. Analysis of the results from WC-1 and Pt-1 indicate that the addition of bicarbonate can stimulate TAG accumulation in both Chlorophytes and diatomaceous algae, and there is possibly a N-dependency for this stimulation. In essence, the results strongly suggest that bicarbonate addition acts as a 'trigger' for TAG accumulation.

Figure 14:
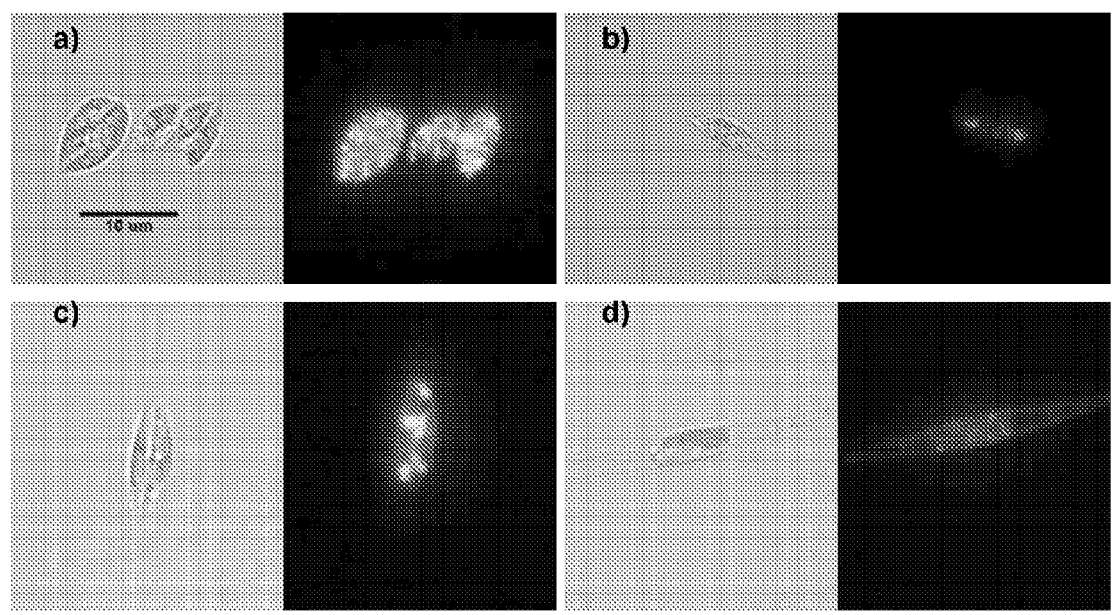
FIG. 14 depicts transmitted micrographs and Nile Red epifluorescent images of *Scenedesmus* WC-1 (top) and *Phaeodactylum tricornutum* Pt-1 (bottom) when bicarbonate was added pre-nitrate depletion (a and c) and when added post-nitrate depletion (b and d). Cells imaged represent average cells for each respective culture and magnification is identical between all images.

FIG. 14 shows optical micrographs and Nile Red epifluorescence images of both WC-1 and Pt-1 when bicarbonate is added pre- or post-nitrate depletion. In the Nile Red epifluorescence images, yellow shows the lipid bodies that have accumulated within the cells. Clearly, the images corroborate the experimental observation of bicarbonate inducing TAG accumulation when added near nitrate depletion. Furthermore, Nile Red has become a generally accepted screening method for analyzing TAG in algal cultures both in academics and industry. Specifically, previous work done with marine diatoms *Amphora coffeaeformis* and *Navicula* sp., which are similar to Pt-1, showed strong correlations between Nile Red fluorescence and gas chromatography analysis of neutral lipids (i.e. TAG) which substantiates our use of Nile Red to monitor cellular TAG accumulation (Cooksey et al. 1987).

Example 10

Sodium Bicarbonate Vs. Sodium Carbonate in WC-1

Figure 15:
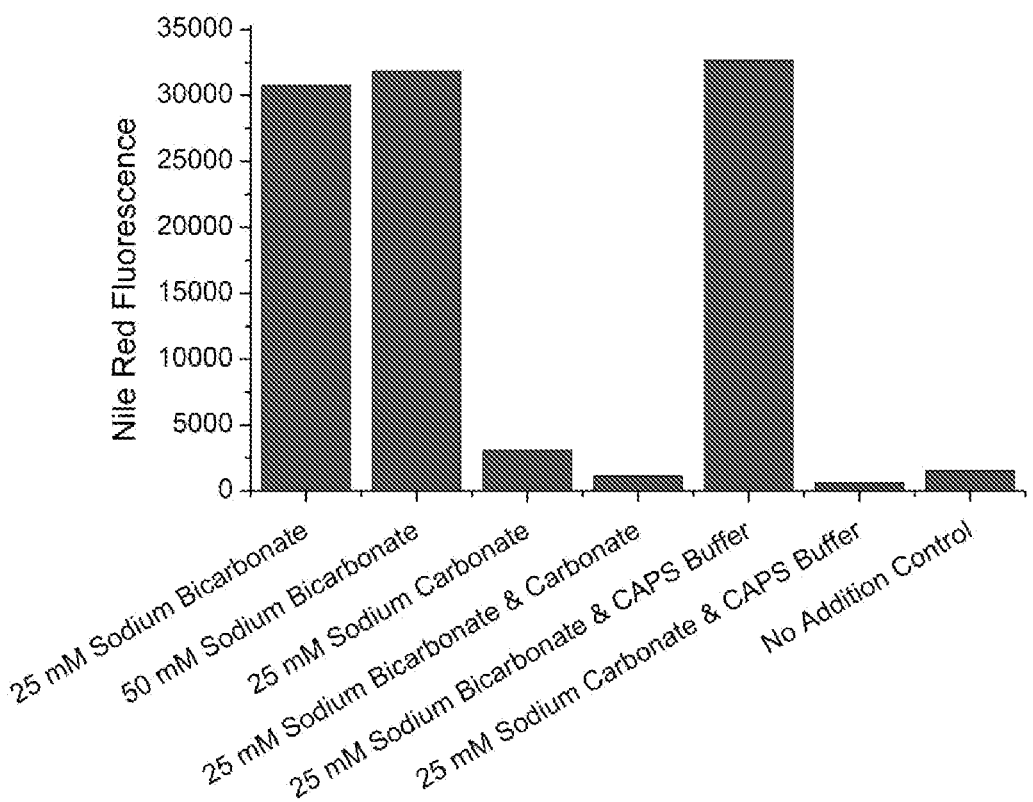
FIG. 15 depicts *Scenedesmus* WC-1 TAG accumulation from sodium bicarbonate and sodium carbonate both as individual, mix, or buffered additives (CAPS Buffer pKa 10.3). Growth was maintained in unbuffered Bold's Basal medium until time of addition just prior to medium nitrate depletion.

Preliminary investigation using NaHCO$_3$ and Na$_2$CO$_3$ has been done on *Scenedesmus* sp. WC-1. FIG. 15 shows that 25 and 50 mM NaHCO$_3$ induce similar levels of TAG when added to unbuffered medium. Similarly, the TAG induction from 25 mM NaHCO$_3$ with 25 mM CAPS buffer (pKa 10.3) (unbuffered previous to addition) is almost identical to the unbuffered additions. In all cases of Na$_2$CO$_3$ addition, WC-1 did not accumulate elevated levels of TAG. Comparison of NaHCO$_3$ and Na$_2$CO$_3$ with CAPS buffer show that elevated TAG was observed due to the bicarbonate ion. Furthermore, by comparing response of 50 mM NaHCO$_3$ and 25 mM Na$_2$CO$_3$ it can be deduced that the Na ion is not major ion in causing elevated TAG, these two additions have equivalent molar concentrations of Na ions. All additions were made near nitrate depletion in the culture medium.

Example 11

Minimal Concentration of Sodium Bicarbonate Needed to Stop Replication in WC-1

Figure 16:
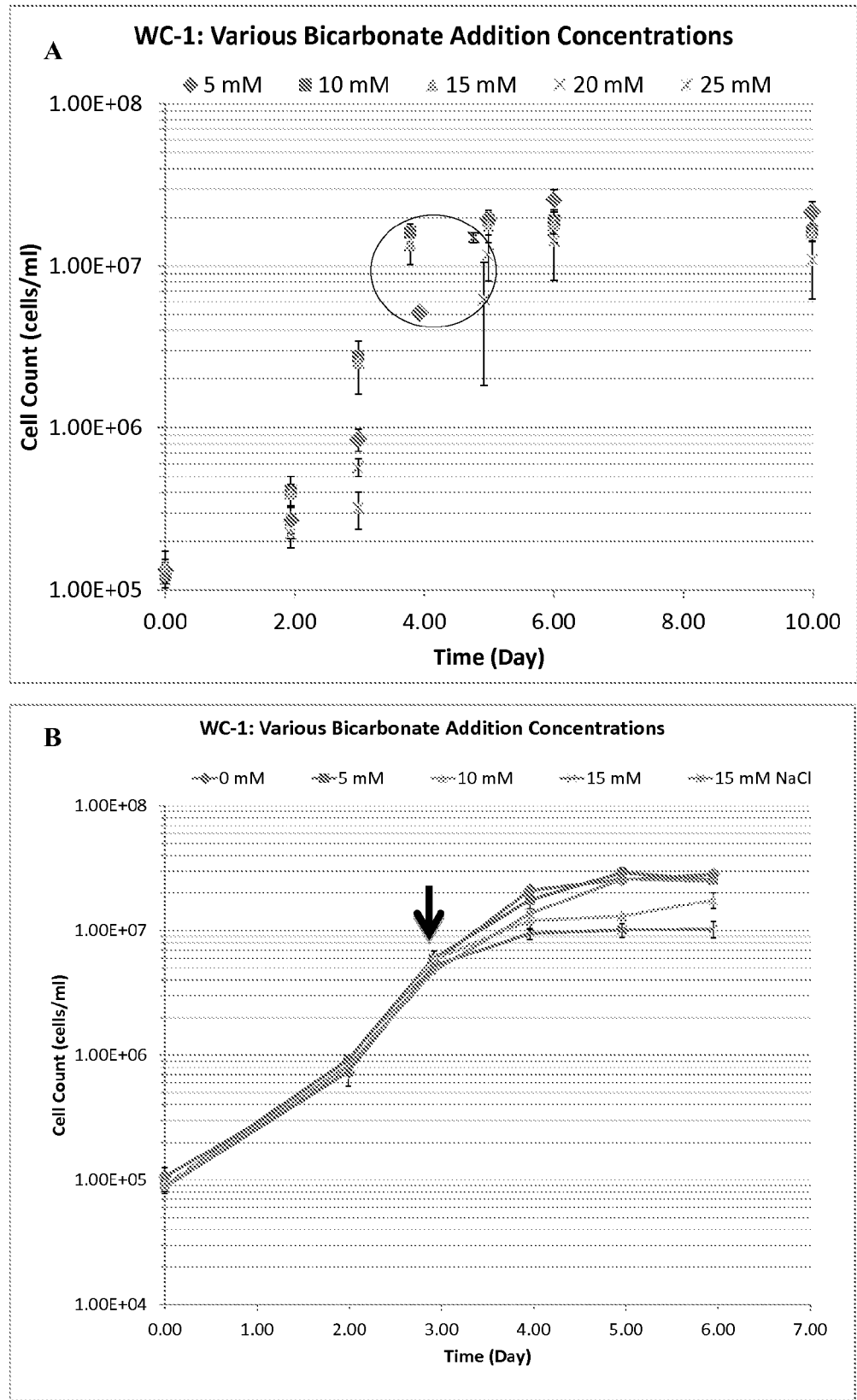
FIG. 16 depicts growth of *Scenedesmus* WC-1 after addition of 5, 10, 15, 20, and 25 mM $NaHCO_3$ (A) and 0, 5, 10, 15 mM $NaHCO_3$ and 15 mM NaCl (B). Time of addition is indicated by the circle (A) and arrow (B).

Initial investigation of how much NaHCO$_3$ is needed to stop cellular replication in WC-1 and thus shift the organism's metabolism into a TAG accumulation state, was performed. FIG. 16 shows the results of 0, 5, 10, 15, 20, and 25 mM NaHCO$_3$ and 15 mM NaCl additions to WC-1 just prior to medium nitrate depletion. Results indicate that 10-15 mM NaHCO$_3$ addition was the minimal concentration range needed to stop cellular replication. Furthermore, cell morphology was monitored by a microscope and cells with less than 10 mM NaHCO$_3$ addition did not indicate cell cycle halting characteristics (as compared with images in FIG. 14).

Example 12

Figure 17:
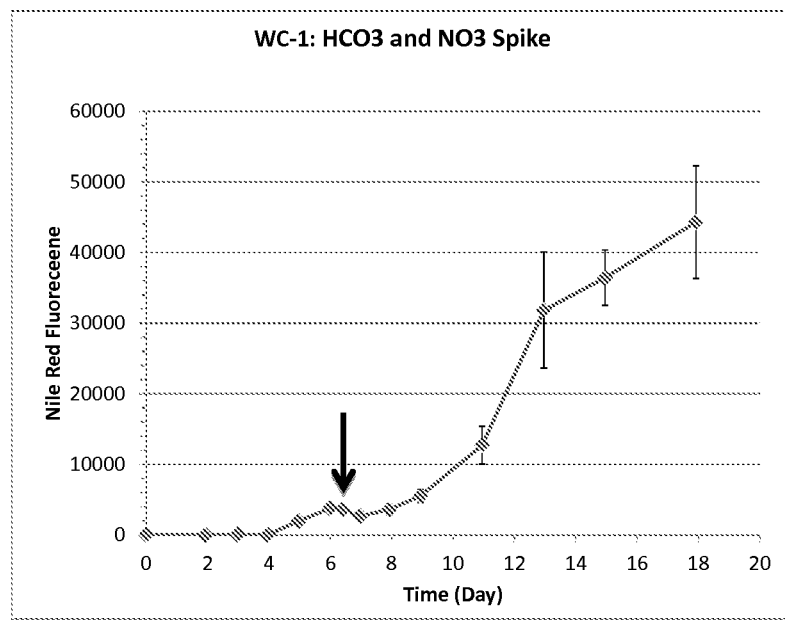
FIG. 17 depicts Nile Red fluorescence of *Scenedesmus* WC-1 when 50 mM $NaHCO_3$ and 180 mM $NO_3$ are added during stationary phase after medium nitrate had been completely consumed. Arrow indicates time of addition.

WC-1 Response to Sodium Bicarbonate and Nitrate Addition Post-Medium Nitrate Depletion Previous data indicated that NaHCO$_3$ addition post-medium nitrate depletion results in a complete loss of cellular TAG accumulation (see FIG. 7). It was hypothesized that medium nitrogen is needed to shift the metabolism of WC-1 into a TAG accumulating state. Therefore, 50 mM NaHCO$_3$ and 180 mM NO$_3$ was added to WC-1 in late stationary phase after medium nitrate had been completely depleted, shown in FIG. 17. The results indicate that the addition mixture resulted in causing TAG accumulation in WC-1. However, the rate of TAG accumulation was not as fast as previously observed (FIG. 7). It was noticed that there is a much higher cell population and more dense cultures when WC-1 is allowed to grow to late stationary phase. It is hypothesized that under these dense conditions, there was probably light limitation which could cause the decrease in TAG accumulation rate.

Example 13

PC-3 Response to Sodium Bicarbonate

The addition of 50 mM NaHCO$_3$ prior to nitrate depletion was tested on *Coelastrella* sp. PC-3. There was no observable increase in TAG accumulation from the bicarbonate addition as measured with Nile Red fluorescence even though cellular replication ceased when the NaHCO$_3$ addition was added (data not shown).

Example 14

EN-2 Response to Sodium Bicarbonate

Figure 18:
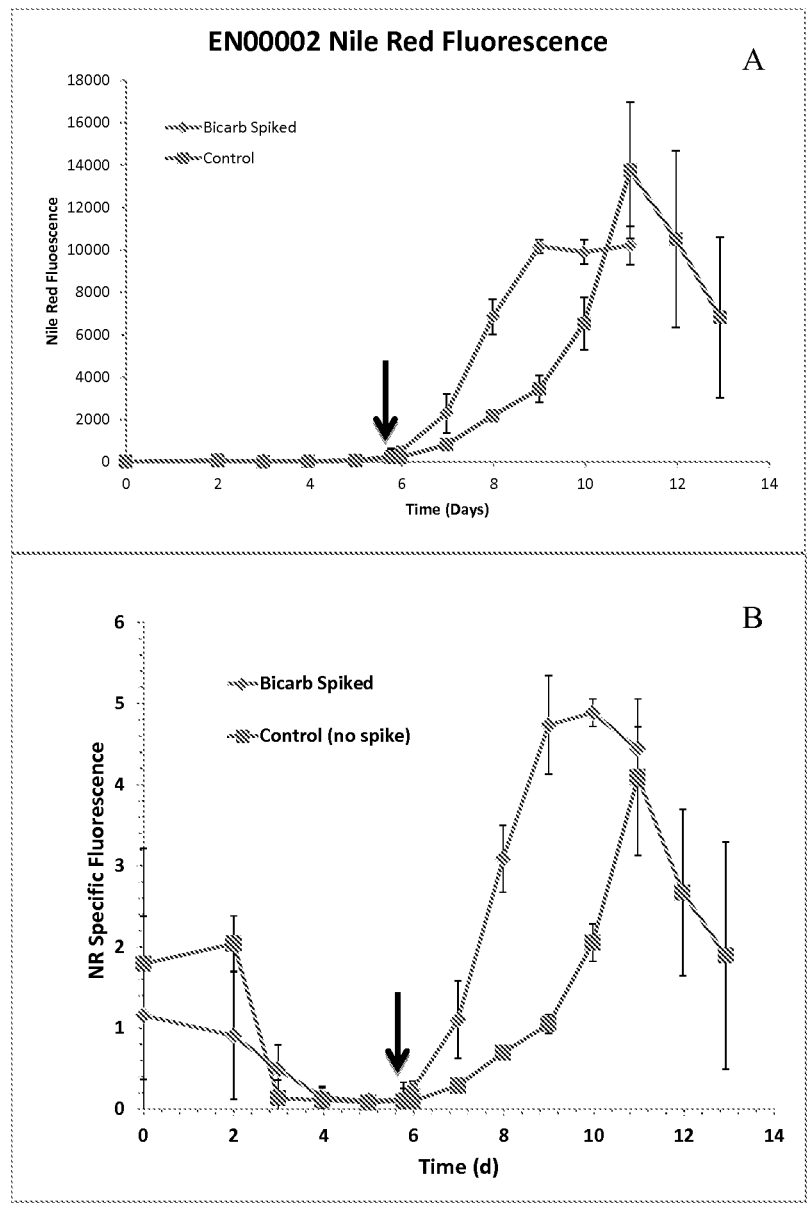
FIG. 18 depicts Nile Red fluorescence (A) and Nile Red specific fluorescence (B) of *Chlorophyta* EN-2 when 50 mM $NaHCO_3$ was added prior to medium nitrate depletion. Nile Red specific fluorescence indicates TAG per cell and is calculated by Nile Red fluorescence×cell number$^{-1}$×10,000 (scaling factor). Arrow indicates time of addition.

The addition of 50 mM NaHCO$_3$ prior to nitrate depletion was tested on *Chlorophyta* sp. EN-2. FIG. 18 shows the Nile Red fluorescence and Nile Red specific fluorescence response, and there was an observable increase in TAG accumulation rate and TAG per cell level (Nile Red specific fluorescence).

Example 15

Figure 19:
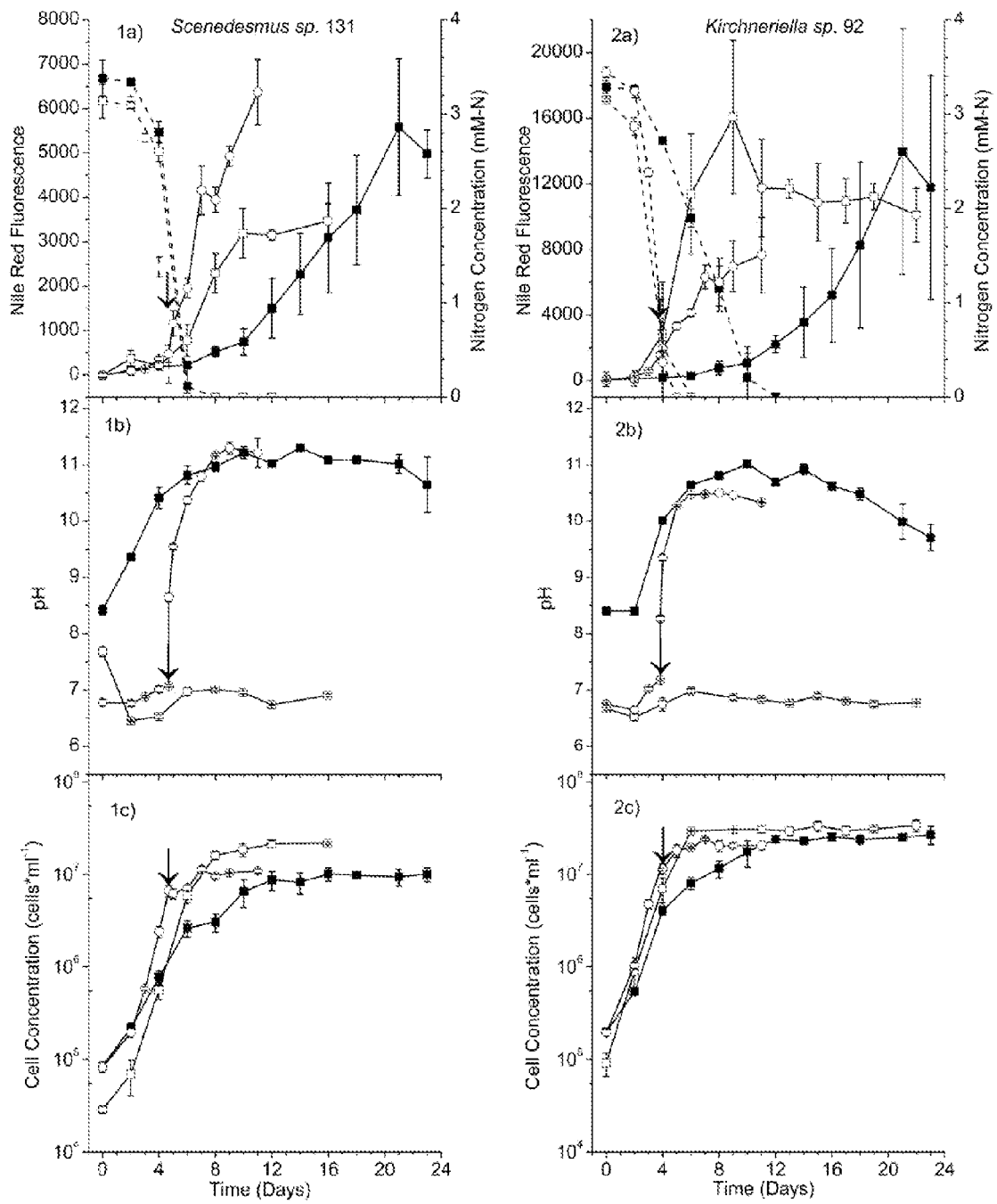
FIG. 19 depicts Nile Red fluorescence (a), pH (b), and average cell density (c) for (1) *Scenedesmus* sp. 131 and (2) *Kirchneriella* sp. 92 grown on nitrate and utilizing 50 mM $NaHCO_3$ addition to cultures grown on 5% CO2 and switched to air (○), no addition growing on 5% CO2 (□), and no addition growing on air (■). Arrow represents time of nitrate addition.

*Scenedesmus* sp. 131 and *Kirchneriella* sp. 92 Responses to Sodium Bicarbonate The addition of 50 mM NaHCO$_3$ prior to nitrate depletion was tested on Chlorophytes *Scenedesmus* sp. 131 and *Kirchneriella* sp. 92. FIG. 19 (top) shows the Nile Red fluorescence of these two organisms when 50 mM NaHCO$_3$ was added prior to nitrate depletion. 131 shows an increase in TAG accumulation rate while 92 shows a decrease in TAG accumulation rate.

Further Information on Experimental Methods

Organism Isolation and Culture.

*Scenedesmus* sp. strain WC-1 (WC-1) was isolated and confirmed unialgal as previously described (Gardner et al. 2010). WC-1 was cultured on Bold's basal medium with pH adjusted to 8.7 with KOH previous to autoclaving (Nichols and Bold 1965). *Phaeodactylum tricornutum* strain Pt-1 (CCMP 2561) (Pt-1) was acquired from The Provasoli-Guillard National Center for Culture of Marine Phytoplankton (CCMP). Pt-1 was cultured on ASP II medium and 50 mM Tris buffer (Sigma-Aldrich, St. Louis Mo.), pKa 7.8 (Provasoli et al. 1957). Both organisms were checked for bacterial contamination by inoculation into respective medium supplemented with 0.05% yeast extract and 0.05% glucose and incubated in the dark. Experiments were conducted in triplicate in batch culture using 70 mm×500 mm glass tubes containing 1 L media submersed in a water bath to control temperature. Rubber stoppers, containing ports for aeration and sampling, were used to seal the tubes. Temperature was maintained at 24° C. and 20° C., ±1° C., for WC-1 and Pt-1, respectively. Light (400 μmoles m$^{-2}$s$^{-1}$) was maintained on a 14:10 light:dark cycle by a T5 light bank. Aeration (400 mL min$^{-1}$) was supplied by humidified compressed air with and without 5% CO$_2$ (v/v) and controlled using individual rotameters on each bioreactor (Cole-Parmer, Vernon Hills Ill.).

Cell concentrations were determined using an optical hemacytometer with a minimum of 400 cells counted for statistical reliability. Light micrographs and Nile Red fluorescence images were taken using a transmitted/epifluorescence light microscope (Nikon Eclipse E800) with an Infinity 2 color camera.

Analysis of Media Components.

Medium pH was measured on samples using a standard bench top pH meter. Nitrate in Bolds basal medium was measured by ion chromatography (IC) using an IonPac AS9-HC Anion-Exchange Column (Dionex) with a 9.0 mM sodium carbonate buffer set at a flow rate of 1.0 mL min$^{-1}$. Detection was performed using a CD20 conductivity detector (Dionex) at 21° C., and IC data was analyzed on Dionex PeakNet 5.2 software. Nitrate in ASP II medium was measured using a colorimetric assay based on the reaction of Czechrome NAS reagent (Polysciences Inc., Warrington Pa.) with nitrate ions. In brief, 1 mL of culture was centrifuged at 16,000 g for 15 minutes. The supernatant liquid was then collected for nitrate quantification. 0.1 mL of sample was gently mixed with 1 mL of reagent solution prepared as described by the manufacturer (Polysciences Inc., Warrington Pa.), and incubated 20 minutes at room temperature. The absorbance was read at 570 nm, and nitrate concentration of the sample was calculated using a nitrate standard curve.

Lipid Analysis.

Cellular TAG accumulation was estimated using the Nile Red (9-diethylamino-5H-benzo(α)phenoxazine-5-one) (Sigma-Aldrich, St. Louis Mo.) fluorescence method (Cooksey et al. 1987). TAG accumulation over time was measured by removing 1 mL aliquots from cultures and assayed directly with Nile Red (4 μL from 250 μL/mL in acetone) or by diluting with 4 mL ultrapure H$_2$O or salt water for WC-1 and Pt-1, respectively, before assaying directly with Nile Red (20 μL from 250 μL/mL in acetone). To maintain linearity of the Nile Red assay, dilution was required when population counts exceeded 1×10$^7$ cell mL$^{-1}$ and 3×10$^6$ cell mL$^{-1}$ for WC-1 and Pt-1, respectively. Total Nile Red fluorescence was quantified on a microplate reader (Bio-Tek, Winooski, Vt.) utilizing 480/580 nm excitation/emission filters. A baseline sensitivity setting of 75 was experimentally determined to maximize the signal-to-noise ratio, while accommodating fluorescent level changes over 10,000 units. To minimize fluorescence spillover, black walled 96-well plates were loaded with 200 μL of sample. Unstained samples were used for background medium and cellular autofluorescence correction. It has been shown (Cooksey et al. 1987) that the Nile Red intensity shifts for different algal strains over time. This was recently reconfirmed (Elsey et al. 2007). Measurement times of 60 min and 3 min after staining were optimal for WC-1 and Pt-1, respectively.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Cunningham, J., *Biofuel joins the jet set.* Professional Engineering, 2007. 20(10): p. 32-32.

2. Hill, J., et al., *Environmental, economic, and energetic costs and benefits of biodiesel and ethanol biofuels*. Proceedings of the National Academy of Sciences of the United States of America, 2006. 103(30): p. 11206-11210.
3. Hu, Q., et al., *Microalgal Triacylglycerols as Feedstocks for Biofuel Production: Perspectives and Advances*. The Plant Journal, 2008. 54(4): p. 621-639.
4. Gardner, R., et al., *Medium pH and Nitrate Concentration Effects on Accumulation of Triacylglycerol in Two Members of the Chlorophyta*. Journal of Applied Phycology, 2010, 1-12, doi:10.1007/s10811-010-9633-4.
5. Sheehan, J., et al., *A Look Back at the United States Department of Energy's Aquatic Species Program—Biodiesel from Algae*. 1998, National Renewable Energy Laboratory: Golden, Colo. p. 328.
6. Stephenson, A., et al., *Influence of nitrogen-limitation regime on the production by Chlorella vulgaris of lipids for biodiesel feedstocks*. Biofuels, 2010. 1(1): p. 47-58.
7. Thomas, R. M. and K. E. Cooksey, *Triglyceride accumulation and the cell cycle in chlorella*. 1990, Montana State University, 1990. p. xi, 132 leaves.
8. Guckert, J. and K. Cooksey, *Triglyceride Accumulation and Fatty Acid Profile Changes in Chlorella (Chlorophyta) During High pH-Induced cell Inhibition*. Journal of Phycology, 1990. 26(1): p. 72-79.
9. Shiraiwa, Y., A. Goyal, and N. E. Tolbert, *Alkalization of the Medium by Unicellular Green Algae during Uptake Dissolved Inorganic Carbon*. Plant and Cell Physiology, 1993. 34(5): p. 649-657.
10. Bozzo, G. G., B. Colman, and Y. Matsuda, *Active transport of CO2 and bicarbonate is induced in response to external CO2 concentration in the green alga Chlorella kessleri*. J. Exp. Bot., 2000. 51(349): p. 1341-1348.
11. Matsuda, Y. and B. Colman, *Induction of CO2 and Bicarbonate Transport in the Green Alga Chlorella ellipsoidea (I. Time Course of Induction of the Two Systems)*. Plant Physiol., 1995. 108(1): p. 247-252.
12. Moroney, J. V. and A. Somanchi, *How Do Algae Concentrate $CO_2$, to Increase the Efficiency of Photosynthetic Carbon Fixation?* Plant Physiology, 1999. 119(1): p. 9-16.
13. Thielmann, J., et al., *Two Systems for Concentrating CO2 and Bicarbonate during Photosynthesis by Scenedesmus*. Plant Physiol., 1990. 92(3): p. 622-629.
14. Lytovchenko, A., U. Sonnewald, A. R. Fernie. (2007). *The complex network of non-cellulosic carbohydrate metabolism*. Current opinion in plant biology. 10(3), 227-235.
15. Schwender, J. J., Y. Ohlrogge, Y. Shachar-Hill. (2004). *Understanding flux in plant metabolic networks*. Current opinion in plant biology. 7(3), 309-317.
16. Allen, D. K., I. G. L. Libourel. Y. Shachar-Hill. (2009). *Metabolic flux analysis in plants: coping with complexity*. Plant, Cell & Environment. 32(9), 1241-1257.
17. Sweetlove, L. J., A. R. Fernie. (2005). *Regulation of metabolic networks: Understanding metabolic complexity in the systems biology era*. New Phytologist. 168(1), 9-24.
18. Arabolaza, A., E. Rodriguez, S. Altabe, H. Alvarez, H. Gramajo. (2008). *Multiple pathways for triacylglycerol biosynthesis in Streptomyces coelicolor*. Applied and Environmental Microbiology. 74(9), 2573-2582.
19. Dahlqvist, A. et al. (2000). *Phospholipid: Diacylglycerol acyltransferase: an enzyme that catalyzes the acyl-CoA-independent formation of triacylglycerol in yeast and plants*. Proceedings of the National Academy of Sciences. 97(12), 6487-6492.
20. Stahl, U. et al. (2004). *Cloning and functional characterization of a phospholipid: Diacylglycerol acyltransferase from arabidopsis*. Plant Physiology 135(3), 1324-1335.
21. Singh et al., 2010a, Mechanism and challenges in commercialisation of algal biofuels, Bioresource Technology, doi:10.1016/j.biortech.2010.06.057
22. Singh et al., 2010b, Commercialization potential of microalgae for biofuels production, Renewable and Sustainable Energy Reviews 14 (2010) 2596-2610
23. Singh et al., 2010c, Renewable fuels from algae: An answer to debatable land based fuels, Bioresource Technology, doi:10.1016/j.biortech.2010.06.032
24. Sims et al., 2010, An overview of second generation biofuel technologies, Bioresource Technology 101 (2010) 1570-1580
25. Demirbas et al., Algae Energy: Algae as a New Source of Biodiesel, Springer 2010, ISBN 1849960496, 9781849960496
26. Khattar et al., Algal Biology and Biotechnology, I. K. International Pvt Ltd, 2009, ISBN 9380026196, 9789380026190
27. Miller et al., Algae Fuel, Alphascript Publishing, 2009, ISBN 6130009720, 9786130009724
28. Chen et al., Review of the biological and engineering aspects of algae to fuels approach, Int J Agric & Biol Eng, Vol. 2 No. 4, pages 1-30
29. Pedersen et al., Nutrient control of algal growth in estuarine waters. Marine Ecology Progress Series, Vol 142: 261-272, 1996.
30. Hasle, G. R.; Syvertsen, E. E. (1997). Marine Diatoms. In: Tomas, C. R. (1997). Identifying Marine Diatoms and Dinoflagellates. Academic Press. pp. 5-385.
31. Round, F. E. and Crawford, R. M. (1990). The Diatoms. Biology and Morphology of the Genera, Cambridge University Press, UK.
32. Canter-Lund, H. and Lund, J. W. G. (1995). Freshwater Algae, Biopress Limited. ISBN 0948737255.
33. Armbrust et al. (2004). The genome of the diatom *Thalassiosira pseudonana*: ecology, evolution, and metabolism. Science 306, 79-86.
34. Bowler, C.; et al. (2008). "The Phaeodactylum genome reveals the evolutionary history of diatom genomes". Nature 456 (7219): 239-244.
35. Martino et al., (2007), Genetic and phenotypic characterization of *Phaeodactylum tricornutum* (Bacillariophyceae) accessions, J. Phycol. 43, 992-1009.
36. Montsant et al., (2005), Comparative Genomics of the Pennate Diatom *Phaeodactylum tricornutum*, Plant Physiology, Vol. 137, pp. 500-513.
37. Beardall, J. (1981). $CO_2$ accumulation by *Chlorella saccharophila* (Chlorophyceae) at low external ph: Evidence for active transport of inorganic carbon at the chloroplast envelope1. Journal of Phycology, 17(4), 371-373, doi: 10.1111/j.1529-8817.1981.tb00864.x.
38. Beardall, J., & Raven, J. A. (1981). Transport of inorganic carbon and the '$CO_2$ concentrating mechanism' in *Chlorella emersonii* (chlorophyceae)1. Journal of Phycology, 17(2), 134-141, doi:10.1111/j.1529-8817.1981.tb00832.x.
39. Bilgen, S., Kaygusuz, K., & Sari, A. (2004). Renewable energy for a clean and sustainable future. Energy Sources, 26(12), 1119-1129.
40. Brennan, L., & Owende, P. (2010). Biofuels from microalgae—a review of technologies for production, processing, and extractions of biofuels and co-products. Renewable & Sustainable Energy Reviews, 14, 21.
41. Brown, L. (2006). Plan b: Rescuing a planet under stress and a civilization in trouble: W.W. Norton Publishing.
42. Chen, W., Zhang, C. W., Song, L. R., Sommerfeld, M., & Hu, Q. (2009). A high throughput Nile Red method for quantitative measurement of neutral lipids in microalgae. Journal of Microbiological Methods, 77(1), 41-47, doi: DOI 10.1016/j.mimet.2009.01.001.
43. Chisti, Y. (2007). Biodiesel from microalgae. Biotechnology Advances, 25(3), 294-306.
44. Colman, B., Huertas, I. E., Bhatti, S., & Dason, J. S. (2002). The diversity of inorganic carbon acquisition mechanisms in eukaryotic microalgae. Functional Plant Biology, 29(3), 261-270.
45. Cooksey, K., Guckert, J., Williams, S., & Callis, P. (1987). Fluorometric determination of the neutral lipid content of microalgal cells using nile red. *Journal of Microbiological Methods*, 6(6), 333-345.
46. Demirbas, M. F. (2010). Microalgae as a feedstock for biodiesel. Energy Education Science and Technology Part a—Energy Science and Research, 25(1-2), 31-43.
47. Demirbas, M. F., Balat, M., & Balat, H. (2009). Potential contribution of biomass to the sustainable energy development. Energy Conversion and Management, 50(7), 1746-1760.
48. Dismukes, G. C., Carrieri, D., Bennette, N., Ananyev, G. M., & Posewitz, M. C. (2008). Aquatic phototrophs: Efficient alternatives to land-based crops for biofuels. Current Opinion in Biotechnology, 19(3), 235-240, doi:DOI 10.1016/j.copbio.2008.05.007.
49. Dukes, J. (2003). Burning buried sunshine: Human consumption of ancient solar energy. Climatic Change, 61(1), 31-44.
50. Elsey, D., Jameson, D., Raleigh, B., & Cooney, M. (2007). Fluorescent measurement of microalgal neutral lipids. Journal of Microbiological Methods, 68(3), 639-642.
51. Francisco, E. C., Neves, D. B., Jacob-Lopes, E., & Franco, T. T. (2010). Microalgae as feedstock for biodiesel production: Carbon dioxide sequestration, lipid production and biofuel quality. Journal of Chemical Technology and Biotechnology, 85(3), 395-403, doi:Doi 10.1002/Jctb.2338.
52. Ghoshal, D., & Goyal, A. (2001). Oxygen inhibition of dissolved inorganic carbon uptake in unicellular green algae. Phycological Research, 49(4), 319-324, doi: 10.1046/j.1440-1835.2001.00247.x.
53. Giordano, M., Beardall, J., & Raven, J. A. (2005). CO2 concentrating mechanisms in algae: Mechanisms, environmental modulation, and evolution. [Article]. Annual Review of Plant Biology, 56(1), 99-131, doi:10.1146/annurev.arplant.56.032604.144052.
54. Goyal, A., & Tolbert, N. E. (1990). Salicylhydroxamic acid (sham) inhibition of the dissolved inorganic carbon concentrating process in unicellular green algae. Plant Physiol., 92(3), 630-636, doi:10.1104/pp. 92.3.630.
55. Greenwell, H., Laurens, L., Shields, R., Lovitt, R., & Flynn, K. (2010). Placing microalgae on the biofuels priority list: A review of the technological challenges. Journal of the Royal Society Interface, 7(46), 703-726, doi:DOI 10.1098/rsif.2009.0322.
56. Guckert, J. B., & Thomas, R. M. (1988). Understanding the regulation of lipid synthesis in *Chlorella*: A preliminary step in the formation of biological fuels. Paper presented at the Symposium on Applied Phycology, Monterey Calif.
57. Kaplan, A., & Reinhold, L. (1999). $CO_2$ concentrating mechanisms in photosynthetic microorganisms. [Article]. Annual Review of Plant Physiology & Plant Molecular Biology, 50(1), 539.
58. Lardon, L., Helìas, A., Sialve, B., Steyer, J.-P., & Bernard, O. (2009). Life-cycle assessment of biodiesel production from microalgae. Environmental Science & Technology, 43(17), 6475-6481, doi:10.1021/es900705j.
59. Lee, S., Yoon, B.-D., & Oh, H.-M. (1998). Rapid method for the determination of lipid from the green alga *Botryococcus braunii*. Biotechnology Techniques, 12(7), 553-556.
60. Mata, T. M., Martins, A. A., & Caetano, N. S. (2010). Microalgae for biodiesel production and other applications: A review. Renewable & Sustainable Energy Reviews, 14(1), 217-232, doi:DOI 10.1016/j.rser.2009.07.020.
61. Moroney, J. V., & Tolbert, N. E. (1985). Inorganic carbon uptake by *Chlamydomonas reinhardtii*. Plant Physiol., 77(2), 253-258, doi:10.1104/pp. 77.2.253.
62. Moroney, J. V., & Ynalvez, R. A. (2007). Proposed carbon dioxide concentrating mechanism in *Chlamydomonas reinhardtii*. Eukaryotic Cell, 6(8), 1251-1259, doi: 10.1128/ec.00064-07.
63. Nichols, H., & Bold, H. (1965). *Trichosarcina polymorpha* gen. Et sp. November Journal of Phycology, 1(1), 34-38.
64. Palmqvist, K., Sjoberg, S., & Samuelsson, G. (1988). Induction of inorganic carbon accumulation in the unicellular green algae *Scenedesmus obliquus* and *Chlamydomonas reinhardtii*. Plant Physiol., 87(2), 437-442, doi: 10.1104/pp. 87.2.437.
65. Posten, C., & Schaub, G. (2009). Microalgae and terrestrial biomass as source for fuels—a process view. Journal of Biotechnology, 142(1), 64-69, doi:DOI 10.1016/j.jbiotec.2009.03.015.
66. Provasoli, L., McLaughlin, J. J. A., & Droop, M. R. (1957). The development of artificial media for marine algae. Archives of Microbiology, 25(4), 392-428.
67. Radmer, R., Ollinger, O. (1980). Light-driven uptake of oxygen, carbon dioxide, and bicarbonate by the green alga *Scenedesmus*. Plant Physiol., 65(4), 723-729, doi:10.1104/pp. 65.4.723.
68. Raven, J. (2010). Inorganic carbon acquisition by eukaryotic algae: Four current questions. Photosynthesis Research, 106(1), 123-134, doi:10.1007/s11120-010-9563-7.
69. Reinfelder, J. R., Milligan, A. J., & Morel, F. M. M. (2004). The role of the C4 pathway in carbon accumulation and fixation in a marine diatom. Plant Physiol., 135(4), 2106-2111, doi:10.1104/pp. 104.041319.
70. Rotatore, C., & Colman, B. (1991). The acquisition and accumulation of inorganic carbon by the unicellular green alga *Chlorella ellipsoidea*. Plant, Cell and Environment, 14(4), 377-382.
71. Schenk, P., Thomas-Hall, S., Stephens, E., Marx, U., Mussgnug, J., Posten, C., et al. (2008). Second generation biofuels: High-efficiency microalgae for biodiesel production. BioEnergy Research, 1(1), 20-43.
72. Tortell, P. D., Reinfelder, J. R., & Morel, F. M. M. (1997). Active uptake of bicarbonate by diatoms. Nature, 390(6657), 243-244.
73. McLaren, J. W., Mykytiuk, A. P., Willie, S, N., Berman, S. S. (1985), Determination of trace metals in seawater by inductively coupled plasma mass spectrometry with preconcentration on silica-immobilized 8-hydroxyquinoline," Anal. Chem. 57 (14), 2907-2911, DOI: 10.1021/ac00291a037.

The invention claimed is:
1. A method of inducing lipid accumulation in an algae growth system, wherein the algae growth system is under light-dark cycling, said method comprising adding a triggering composition when algae cells in the growth system are in exponential growth stage, but prior to nutrient depletion of the growth system, wherein said triggering composition comprises bicarbonate, and/or one or more compounds that provide bicarbonate after the composition is added into the algae growth system, and wherein algae replication in the growth system is inhibited at the time when the triggering composition is added.

2. The method of claim 1, wherein the inhibition happens during late phase of the exponential growth of algae in the system.

3. The method of claim 1, wherein the triggering composition further comprises one or more agents that increase the pH of the algae growth system.

4. The method of claim 1, wherein the inhibition comprises an aeration shift of $CO_2$ concentration in the growth system from high to low, wherein the shift is sufficient to inhibit algae replication.

5. The method of claim 1, wherein the algae is a *Scenedesmus* sp., a *Chlorophyta* sp. or a diatom.

6. The method of claim 1, wherein the triggering composition increases the pH of the algae growth system to at least pH 9.5.

7. The method of claim 1, wherein the triggering composition provides the algae growth system a concentration of bicarbonate of at least 10 mM.

8. The method of claim 1, wherein the triggering composition is added into the growth system as close to nutrient depletion of the growth system as possible.

9. The method of claim 1, wherein the lipid is triacylglycerol (TAG).

10. The method of claim 1, wherein the lipid accumulation in the algae growth system is at least 5 times the lipid accumulation in a control algae growth system in which said triggering composition is not added.

\* \* \* \* \*